United States Patent
Colland et al.

(10) Patent No.: US 9,546,150 B2
(45) Date of Patent: Jan. 17, 2017

(54) SUBSTITUTED QUINAZOLIN-4-ONES FOR INHIBITING UBIQUITIN SPECIFIC PROTEASE 7

(75) Inventors: Frédéric Colland, Puiseux en France (FR); Marie-Edith Gourdel, Savigny le Temple (FR)

(73) Assignee: HYBRIGENICS SA, Paris (FR)

( * ) Notice: Subject to any disclaimer, the term of this patent is extended or adjusted under 35 U.S.C. 154(b) by 0 days.

(21) Appl. No.: 14/241,923

(22) PCT Filed: Aug. 29, 2012

(86) PCT No.: PCT/EP2012/066741
§ 371 (c)(1),
(2), (4) Date: Jun. 16, 2014

(87) PCT Pub. No.: WO2013/030218
PCT Pub. Date: Mar. 7, 2013

(65) Prior Publication Data
US 2014/0371247 A1 Dec. 18, 2014

(30) Foreign Application Priority Data
Sep. 2, 2011 (EP) .................................... 11306096

(51) Int. Cl.
*A61K 31/517* (2006.01)
*C07D 239/88* (2006.01)
*C07D 401/06* (2006.01)
*C07D 409/14* (2006.01)
*C07D 239/91* (2006.01)
*A61K 45/06* (2006.01)

(52) U.S. Cl.
CPC ........... *C07D 401/06* (2013.01); *A61K 31/517* (2013.01); *A61K 45/06* (2013.01); *C07D 239/88* (2013.01); *C07D 239/91* (2013.01); *C07D 409/14* (2013.01)

(58) Field of Classification Search
CPC ........................... A61K 31/517; C07D 239/88
USPC .......... 514/266.3; 544/287; 546/199; 549/59
See application file for complete search history.

(56) References Cited

U.S. PATENT DOCUMENTS

| | | | |
|---|---|---|---|
| 2,796,417 | A | 6/1957 | Randall et al. |
| 3,073,826 | A | 1/1963 | Scarborough |
| 5,100,901 | A | 3/1992 | Sugimoto et al. |
| 8,084,459 | B2 | 12/2011 | Kok et al. |
| 8,163,760 | B2 | 4/2012 | Bush et al. |
| 2005/0095360 | A1 | 5/2005 | Li et al. |
| 2007/0123543 | A1 | 5/2007 | Hossain et al. |
| 2008/0188498 | A1 | 8/2008 | Zhu |
| 2009/0118261 | A1 | 5/2009 | Aquila et al. |
| 2010/0069393 | A1 | 3/2010 | Bush et al. |
| 2011/0263532 | A1 | 10/2011 | Keller et al. |

FOREIGN PATENT DOCUMENTS

| | | |
|---|---|---|
| EP | 1 749 822 | 8/2005 |
| WO | WO-93/12795 | 7/1993 |
| WO | WO-2006/012577 | 2/2006 |
| WO | WO 2006/072048 | 7/2006 |
| WO | WO 2011/086178 | 7/2011 |
| WO | WO 2013/030218 | * 3/2013 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/EP2012/066741 dated Nov. 28, 2012.
Written Opinion for PCT/EP2012/066741 dated Nov. 28, 2012.
Database Registry [Online] Chemical Abstracts Service, Columbus, Ohio, US; (Mar. 25, 2010), XP002675270,retrieved from STN Database accession No. 1214606-92-4 (RN).
Database Registry [Online] Chemical Abstracts Service, Columbus, Ohio, US; (Mar. 25, 2010), XP002675271, retrieved from STN Database accession No. 1214488-43-3 (RN).
Database Registry [Online] Chemical Abstracts Service, Columbus, Ohio, US; (Jul. 5, 2012), XP002687753, retrieved from STN Database accession No. 1381736-63-5 (RN).
Database Registry [Online] Chemical Abstracts Service, Columbus, Ohio, US; (Jul. 5, 2012), XP002687754, retrieved from STN Database accession No. 1381604-36-9 (RN).
Database Registry [Online] Chemical Abstracts Service, Columbus, Ohio, US; (Jul. 4, 2012), XP002687755, retrieved from STN Database accession No. 1381359-12-1 (RN).
Database Registry [Online] Chemical Abstracts Service, Columbus, Ohio, US; (Jul. 4, 2012), XP002687756, retrieved from STN Database accession No. 1381217-56-6 (RN).
Fishman, et al. Journal of Heterocyclic Chemistry, Wileyblackwell Publishing, Inc, US, vol. 5, No. 5, (Aug. 1968), pp. 467-469.
Wolfgang Sippl, et al. "Ubiquitin-specific proteases as cancer drug targets", Future Oncology, Future Medicine Ltd., London, GB, vol. 7, No. 5, (May 2001), pp. 619-632.
Meulmeester, et al., "Loss of HAUSP-Mediated Deubiquitination Contributes to DNA Damage-Induced Destabilization of Hdmx and Hdm2", May 27, 2005, pp. 565-576, vol. 18, Molecular Cell.

(Continued)

*Primary Examiner* — Douglas M Willis
(74) *Attorney, Agent, or Firm* — B. Aaron Schulman, Esq.; Stites & Harbison, PLLC

(57) ABSTRACT

The present invention relates to quinazolin-4-one compounds of formula (I'), their process of preparation and uses thereof. These compounds are useful as selective and reversible inhibitors of ubiquitin specific proteases, particularly USP7, for treating e.g. cancer, neurodegenerative diseases, inflammatory disorders and viral infections.

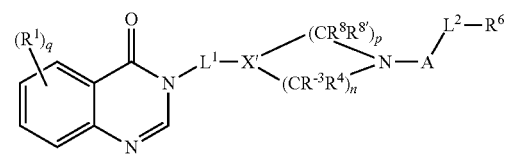

(I')

23 Claims, 6 Drawing Sheets

(56) References Cited

OTHER PUBLICATIONS

Van der Horst, et al. "FOX04 transcriptional activity is regularted by monoubiquitination and USP7/HAUSP", Oct. 2006, pp. 1064-1079, vol. 8, No. 10, Nature Cell Biology.
Nijman, et al, "A Genomic and Functional Inventory of Deubiquitinating Enzymes" Dec. 2, 2005, pp. 773-786, Cell 123.
Hoeller, et al "Ubiquitin and ubiquitin-like proteins in cancer pathogenesis", Oct. 2006, pp. 776-788, vol. 6, www.nature.com/reviews/cancer, Nature Publishing Company.
Rubinsztein, et al. "The roles of intracellular protein-degradation pathways in neurodegeneration", Oct. 19, 2006, pp. 780-786, vol. 443, Insight Review.
Marchenko, et al. "Monoubiquitylation promotes mitochondrial p53 translocation", 2007, pp. 923-934, vol. 26, The EMBO Journal.
Becker, et al., "A role of HAUSP in tumor suppression in a human colon carcinoma xenograft model", May 1, 2008, pp. 1205-1213, vol. 7, No. 9, Cell Cycle.
Song, et al., "The deubiquitinylation and localization of PTEN are regulated by a HAUSP-PML network", Oct. 9, 2008, pp. 813-818, vol. 455, Nature.
Du, et al., "DNMT1 Stability is Regulated by Proteins Coordinating Deubiquitination and Acetylation-Driven Ubiquitination" Nov. 2, 2010, pp. 110, vol. 3, No. 146, Science Signaling.
Epping, et al., "TSPYL5 suppresses p53 levels and function by physical interaction with USP7", Jan. 2011, pp. 102-108, vol. 13, No. 1, Nature Cell Biology.
Colland, Frederic, "The therapeutic potential of deubiquitinating enzyme inhibitors", 2010, pp. 137-143, vol. 38, Biochem. Soc. Trans.
Gao, et al, "The ubiquitin-proteasome pathway in viral infections", 2006, pp. 514, vol. 84, Can. J. Physiol. Pharmacol.
Cummins, et al., "HAUSP is Required for p53 Destabilization", Jun. 2004, pp. 689-692, vol. 3, No. 6, Cell Cycle.
Adams, Julian, "The Proteasome: A suitable antineoplastic target", May 2004, pp. 349-360, vol. 4, Nature Reviews Cancer.
Li, et al., "A Dynamic Role of HAUSP in the p53-Mdm2 Pathway", Mar. 26, 2004, pp. 879-886, vol. 13, Molecular Cell.
Daviet, et al., "Targeting ubiquitin specific proteases for drug discovery", 2008, pp. 270-283, vol. 90, Biochimie.
Everett, et al., "The Ability of Herpes Simplex Virus Type 1 Immediate-Early Protein Vmw110 to Bind to a Ubiquitin-Specific Protease Contributes to Its Roles in the Activation of Gene Expression and Stimulation of Virus Replication" Jan. 1999, pp. 417-426, vol. 73, No. 1, Journal of Virology.
Li, et al., "Deubiquitination of p53 by HAUSP is an important pathway for p53 stabilization", Mar. 2002, pp. 648-653, Nature.
Holowaty, et al., "Protein Interaction Domains of the Ubiquitin-specific Protease, USP7/HAUSP", Nov. 28, 2003, pp. 47753-47761, vol. 278, No. 48, The Journal of Biological Chemistry.
Komander, et al., "Breaking the chains: structure and function of the deubiquitinases" Aug. 2009, pp. 550-563, vol. 10, Nature.
Maertens, et al., "Ubiquitin-specific proteases 7 and 11 modulate Polycomb regulation of the INK4a tumour suppressor", 2010, pp. 2553-2565, vol. 29, The EMBO Journal.
Holowaty, et al., "Protein Profiling with Epstein-Barr Nuclear Antigen-1 Reveals an Interaction with the Herpesvirus-associated Ubiquitin-specific Protease HAUSP/USP7", Aug. 8, 2003, pp. 29987-29994, vol. 278, No. 32, The Journal of Biological Chemistry.
Faustrup, et al., "USP7 counteracts $SCF^{\beta TrCP}$-but not $APC^{Cdh1}$-mediated proteolysis of Claspin" Jan. 5, 2009, pp. 133-19, JCB: Report.
Colland, et al., "Small-molecule inhibitor of USP7/HAUSP ubiquitin protease stabilizes and activates p53 in cells" Aug. 2009, pp. 2286-2295, vol. 8, No. 8, Mol. Cancer Ther.
Li, et al., "Disruption of HAUSP gene stabilizes p53", 2002, pp. 648-653, No. 416, Nature.
Sippl, et al., "Ubiquitin-specific proteases as cancer drug targets", 2011, pp. 619-632, vol. 7, No. 5, Future Oncol.

Summary of Chinese Official Action in corresponding Chinese Application No. 2012800541482.
Partial European Search Report dated Jun. 12, 2012 in corresponding European Application No. 11 30 6096.
European Search Report dated Sep. 27, 2012 in corresponding European Application No. 11 30 6096.
Zhu, et al., "Synthesis and evaluation of 4-quinazolinone compounds as potential antimalarial agents", 2010, pp. 3864-3869, 45, European Journal of Medicinal Chemistry.
Hutchings, et al., "An Antimalarial Alkaloid From Hydrangea III. Degradation", 1952 ,pp. 19-34, vol. 17, No. 1, Journal of Organic Chemistry, American Chemical Society, Easton, US.
Cheng, et al., "Expression of HAUSP in gliomas correlates with disease progression and survival of patients", 2013, pp. 1730-1736, vo. 29, Oncology Reports.
Ching, et al., "A Ubiquitin-specific Protease Possesses a Decisive Role for Adenovirus Replication and Oncogene-mediated Transformation", Mar. 2013, pp. 1-18, vol. 9, No. 3, PLOS Pathogens.
Everett, et al., "A novel ubiquitin-specific protease is dynamically associated with the PML nuclear domain and binds to a herpesvirus regulatory protein", 1997, pp. 1519-1530, vol. 16, No. 7, The EMBO Journal.
Cai, et al., "Ubiquitin-Specific Protease 7 Accelerates $p14^{ARF}$ Degradation by Deubiquitinating Thyroid Hormone Receptor-Interacting Protein 12 and Promotes Hepatocellular Carcinoma Progression", May 2015, pp. 1603-1614.
Huang, et al, "Deubiquitinase HAUSP Stabilizes Rest and Promotes Maintenance of Neural Progenitor Cells", Feb. 2011, pp. 142-152, vol. 13, No. 2, Nat Cell Biol.
Giovinazzi, et al, "USP7 and Daxx regulate mitosis progression and taxane sensitivity by affecting stability of Aurora-A kinase", 2013, pp. 721-731, vol. 20, Cell Death and Differentiation.
Hong, et al, "USP7, a Ubiquitin-Specific Protease, Interacts with Ataxin-1, the SCA1 Gene Product", 2002, pp. 298-306, vol. 20, Molecular and Cellular Neuroscience.
Huether, et al., "The landscape of somatic mutations in epigenetic regulators across 1000 pediatric cancer genomes", Aug. 1, 2014, pp. 1-16, vol. 5, Nat Commun.
Jager, et al, "The Ubiquitin-Specific Protease USP7 Modulates the Replication of Kaposi's Sarcoma-Associated Herpesvirus Latent Episomal DNA", Jun. 2012, pp. 6745-6757, vol. 86, No. 12, Journal of Virology.
Chen, et al., "The Deubiquitinating Enzyme USP7 Regulates Androgen Receptor Activity by Modulating Its Binding to Chromatin", Jul. 14, 2015, pp. 1-29, J. Biol. Chem.
Holowaty, et al., "Protein Profiling with Epstein-Barr Nuclear Antigen-1 Reveals an Interaction with the Herpesvirus-associated Ubiquitin-specific Protease HAUSP/USP7", 2003, pp. 29987-29994, vol. 278, No. 32, Issue of Aug. 8, The Journal of Biological Chemistry.
Meredith, et al., "Herpes Simplex Virus Type 1 Immediate-Early Protein Vmw110 Binds Strongly and Specifically to a 135-kDa Cellular Protein", 1994, pp. 457-469, vol. 200, Virology.
Zhao, et al, "USP7 overexpression predicts a poor prognosis in lung squamous cell carcinoma and large cell carcinoma", 2015, pp. 1721-1729, vol. 36, Tumor Biol.
Salsman, et al., "Proteomic Profiling of the Human Cytomegalovirus UL35 Gene Products Reveals a Role for UL35 in the DNA Repair Response", 2011, pp. 806-820, Journal of Virology.
Nicholson, et al., "The Multifaceted Roles of USP7: New Therapeutic Opportunities", 2011, pp. 61-68, vol. 60, Cell Biochem Biophys.
Zhi, et al., "STAT3 repressed USP7 expression is crucial for colon cancer development", 2012, pp. 3013-3017, FEBS Letters 586.
Morotti, et al., "BCR-ABL disrupts PTEN nuclear-cytoplasmic shuttling through phosphorylation-dependent activation of HAUSP", 2014, pp. 1326-1333, vol. 28, Leukemia.
Noguera, et al, "Nucleophosmin/B26 regulates PTEN through interaction with HAUSP in acute myeloid leukemia", 2013, pp. 1037-1043, vol. 27, Leukemia.

* cited by examiner

```
                        SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
cgtggatcca tgcagatctt tgtgaagacc ctc                                 33

<210> SEQ ID NO 2
<211> LENGTH: 53
<212> TYPE: DNA
<213> ORGANISM: Artificial Sequence
<220> FEATURE:
<223> OTHER INFORMATION: Primer

<400> SEQUENCE: 2
gcgaattctt tatcgtcatc gtctttgtag tctttgacct tcttcttggg acg            53
```

SUBSTITUTED QUINAZOLIN-4-ONES FOR INHIBITING UBIQUITIN SPECIFIC PROTEASE 7

FIELD OF THE INVENTION

The present invention concerns the discovery of new selective and reversible inhibitors of ubiquitin specific proteases, their process of preparation and their therapeutic use.

BACKGROUND OF THE INVENTION

Ubiquitin specific proteases (USP) are cysteines proteases which belong to the deubiquitinating enzymes (DUBs) family.

Deregulation of the ubiquitin-proteasome system has been implicated in the pathogenesis of many human diseases, including cancer (Hoeller et al. *Nat Rev Cancer* 2006, 6(10), 776-788), neurodegenerative disorders (Rubinsztein, *Nature* 2006, 443(7113), 780-786) and viral diseases (Gao & Luo *Can J Physiol Pharmacol* 2006, 84(1), 5-14). The market success of the proteasome inhibitor Velcade® (bortezomib) for the treatment of multiple myeloma and mantle cell lymphoma has established this system as a valid target for cancer treatment (Adams, *Nat Rev Cancer* 2004, 4(5), 349-360). A promising alternative to targeting the proteasome itself would be to interfere with the upstream ubiquitin conjugation/deconjugation machinery, to generate more specific, less toxic anticancer agents.

Mono- and polyubiquitination can be reversed by deubiquitinating enzymes, which specifically cleave the isopeptide bond at the C-terminus of ubiquitin. Ubiquitin specific proteases and ubiquitin C-terminal hydrolases (UCH) enzymes are the best characterized members of the DUB family (Komander et al. *Nat. Rev. Mol. Cell Biol.* 2009, 10(8), 550-63; Nijman et al. *Cell* 2005, 123(5), 773-786). UCHs are thought to cleave small protein substrates preferentially and to be involved principally in the processing and recycling of ubiquitin, but their specific functions remain poorly understood. USPs constitute the largest sub-family of DUBs, with more than 60 members. They remove ubiquitin from specific protein substrates, thus preventing their targeting to the proteasome or regulating their subcellular localization and activation (Daviet & Colland, *Biochimie* 2008, 90(2), 270-83). USPs are emerging as potential targets for pharmacological interference with the ubiquitin regulation machinery, based on their protease activity and involvement in several human diseases (Colland, *Biochem Soc Trans* 2010, 38, 137-43).

USP7 (Ubiquitin Specific Protease 7)/HAUSP (Herpes Associated Ubiquitin Specific Protease) is a 135 kDa protein of the USP family. USP7 has been shown to interact with viral proteins, such as ICP0 (Vmw 110), a herpes simplex virus immediate-early gene stimulating initiation of the viral lytic cycle (Everett et al., *J Virol* 73, 1999, 417-426), and EBNA1 (Epstein-Barr Nuclear Antigen-1) (Holowaty et al., *J Biol Chem* 2003, 278, 29987-29994 and 47753-47761). Human proteins, such as p53 and the major E3 ligase of p53, Mdm2, have also been identified as partners and substrates of USP7 (Cummins et al. *Nature* 2004, 486, Cummins & Vogelstein, *Cell Cycle,* 2004, 3, 689-692; Li et al. *Mol Cell* 2004, 13, 879-886; Li et al. *Nature* 2002, 416, 648-653). More generally USP7 can deubiquitinate different targets, including Mdm2 and p53, and the net deubiquitination of these latter targets ultimately determines functional p53 levels. Consistent with recent reports, USP7 silencing has also been shown to increase steady-state p53 levels by promoting Mdm2 degradation. Binding of USP7 to p53 was recently shown to be regulated by TSPYL5, a protein potentially involved in breast oncogenesis through a competition with p53 for binding to the same region of USP7 (Epping et al., *Nat Cell Biol.* 2011, 13(1):102-8). More recently, both upregulation and downregulation of USP7 have been shown to inhibit colon cancer cell proliferation in vitro and tumor growth in vivo, by resulting in constitutively high p53 levels (Becker et al. *Cell Cycle* 2008, 7(9), 1205-13).

USP7 also alters the level of the p16$^{INK4a}$ tumor suppressor through Bmi1/Me118 stabilization (Maertens et al., *Embo J.* 2010, 29, 2553-2565). Additional proteins involved in genomic integrityregulation such as the DNMT1 DNA methylase and the Claspin adaptor are also stabilized by USP7 (Du et al., *Science Signaling* 2010, 3(146):ra80; Faustrup et al., *J. Cell Biol.* 2009, 184(1):13-9). Importantly, the abundance of USP7 and DNMT1, a protein involved in maintaining epigenetic methylation required to silence genes involved in development and cancer, correlates in human colon cancer (Du et al., *Science Signaling,* 2010, 3(146):ra80). USP7 has also been shown in human cells to deubiquitinate the well-known tumor suppressor gene PTEN, which provokes its nuclear export and hence its inactivation (Song et al., *Nature* 2008, 455(7214), 813-7). More importantly, USP7 overexpression was reported for the first time in prostate cancer and this overexpression was directly associated with tumour aggressiveness (Song et al., *Nature* 2008, 455(7214), 813-7).

USP7 has also been shown in human cells to deubiquitinate FOXO4, which provokes its nuclear export and hence its inactivation; consequently the oncogenic PI3K/PKB signaling pathway was activated (van der Horst et al., *Nat Cell Biol.* 2006, 8, 1064-1073) Finally, USP7 plays an important role in p53-mediated cellular responses to various types of stress, such as DNA damage and oxidative stress (Marchenko et al., *Embo J.* 2007 26, 923-934, Meulmeester et al., *Mol Cell* 2005, 18, 565-576, van der Horst et al., *Nat Cell Biol.* 2006, 8, 1064-1073).

Synthetic inhibitors of USP7 protein binding containing the polypeptide portion P$^1$-Gly-P$^3$-Ser, where P$^1$ is a glutamic acid residue or an amino acid with a non polar side chain and P$^3$ is a glycine residue or an amino acid with non polar side chain, have been reported (WO2006072048).

The phenotypes associated with USP7 silencing and the known connections between USP7 and essential viral proteins and oncogenic pathways, such as the p53/Mdm2 and PI3K/PKB pathways, strongly suggest that targeting USP7 with small-molecule inhibitors may be beneficial in the treatment of cancers and viral diseases (Sippl et al., *Future Oncology* 2011, 7, 619-32). Inhibitors against USP7 were recently reported (Colland et al. *Molecular Cancer Therapeutics* 2009, 8, 2286-95 and EP 1 749 822 and PCT/EP2011/050523.2).

However, to date, no specific and reversible USP7 small molecule inhibitors seem to have been reported.

SUMMARY OF THE INVENTION

According to a first object, the present invention concerns a compound of formula (I):

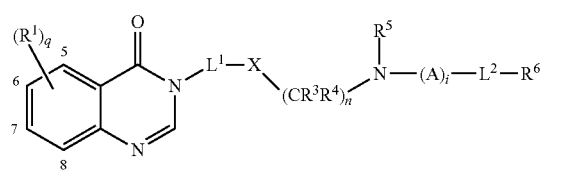

wherein
$R^1$, each identical or different, is chosen from the group consisting of halogen, R, OR, NRR', CN, $CF_3$, C(O)R, C(O)OR, C(O)NRR', $NO_2$, $(C_1-C_6)$alkylene-OR, $(C_1-C_6)$alkylene-NRR', $(C_1-C_6)$alkylene-$CO_2$R, $(C_1-C_6)$alkylene-C(O)NRR', —O—$(C_1-C_6)$alkylene-$CO_2$R, —O—$(C_1-C_6)$alkylene-C(O)NRR', $CO_2$—$(C_1-C_6)$alkylene-OR, $CO_2$—$(C_1-C_6)$alkylene-NRR', C(O)NH—$(C_1-C_6)$alkylene-OR, C(O)NH—$(C_1-C_6)$alkylene-NRR', $OCF_3$, $SO_2R$, $SO_3H$, $SO_2NRR'$, $NHSO_2R$, $R^{10}C\equiv CR^{11}$, $(R^{10})(R^{11})C=C(R^{11})_2$, $(C_1-C_6)$alkylene-C(O)R, NHC(O)R, or $(C_1-C_6)$alkyl interrupted by at least one heteroatom, preferably chosen among O, N or S, preferably O;

$L^1$ is linear or branched $(C_1-C_6)$alkylene optionally substituted by one or more of =O, CN, C(O)R, C(O)OR, or C(O)NRR', or linear or branched $CH_2(C_1-C_6)$alkylene, wherein the later $(C_1-C_6)$alkylene is optionally substituted by one or more of halogen, OR, NRR' or $CF_3$;

X is $CR^2R^7$, $NR^2$, aryl, heteroaryl, cycloalkyl or heterocycle, wherein the aryl, heteroaryl, cycloalkyl or heterocycle is optionally substituted by one or more of linear or branched $C_1-C_6$(alkyl), halogen, OR, NRR', CN, $CF_3$, C(O)R, C(O)OR or C(O)NRR';

$R^2$ is a linear or branched $(C_1-C_6)$alkylene and is linked together with $R^5$=linear or branched $(C_1-C_6)$alkylene to form with —X—$(CR^3R^4)_n$—N—, to which they are attached, an heterocycle, preferably a heterocycle having 5 to 7 members, optionally substituted by one or more of OR, linear or branched $(C_1-C_6)$alkyl, halogen, NRR', CN, $CF_3$, C(O)R, C(O)OR, C(O)NRR', or =O;

$R^5$, is chosen among H and linear or branched $(C_1-C_6)$alkyl, $(C_1-C_6)$alkylene;

$R^3$, $R^4$, each identical or different, are chosen in the group consisting of H, linear or branched $(C_1-C_6)$alkyl, halogen, OR, NRR', CN, $CF_3$, C(O)R, C(O)OR, C(O)NRR' or =O;

q is 0, 1, 2, 3 or 4
n is 0, 1, 2 or 3;
$R^7$ is OR, H, halogen, linear or branched $(C_1-C_6)$alkyl-OR, C(O)OR, C(O)NRR', CN, $OR^9$, NRR' or SR;
i is either 0 or 1;
A is chosen from the group consisting of:
linear or branched —$[C_1-C_6(alkyl)]_{0-1}$-C(O)—;
linear or branched —$[C_1-C_6(alkyl)]_{0-1}$-C(O)NH—;
linear or branched —$[C_1-C_6(alkyl)]_{0-1}SO_2$—; or
linear or branched —$[C_1-C_6(alkyl)]_{0-1}SO_2N$—;
$L^2$ is linear or branched $(C_1-C_6)$alkylene-O or a linear or branched $(C_1-C_6)$alkylene optionally interrupted by at least one heteroatom chosen from O, NR or S and/or optionally substituted by: R, OR, NRR', $(C_1-C_6)$alkyl-OR, $(C_1-C_6)$alkyl-NRR', OC(O)R, NHC(O)R, NHC(O)NRR', CN, C(=NH)NHOR;

$R^6$ is chosen from the group consisting in aryl, heteroaryl, cycloalkyl, heterocycle, H, wherein the aryl, heteroaryl, cycloalkyl or heterocycle is mono or polycyclic and is optionally substituted by one or more of linear or branched $(C_1-C_6)$alkyl, halogen, NRR', CN, $CF_3$, OR, =O, C(O)R, C(O)OR, NHC(O)R, OC(O)R, linear or branched $(C_2-C_6)$alkenylene or C(O)NRR';

$R^9$ is chosen from the group consisting of —C(O)R, —C(O)NHR, —C(O)OR, —C(O)$CH_2$—NRR', —C(O)—$CH_2$—$CH_2$—$CO_2$R, —C(O)—$CH_2$—$SO_3H$, —C(O)—$(C_5H_4N)$, —$PO_3H_2$, or their ionized form;

$R^{10}$ independently identical or different is chosen from a bond, a linear or branched $(C_1-C_6)$alkyl;

$R^{11}$ independently identical or different is chosen from an hydrogen atom, a linear or branched $(C_1-C_6)$alkyl or an aryl, the alkyl or aryl is optionally substituted by OH, $NH_2$, C(O)OH or C(O)$NH_2$;

each R and R', identical or different, are independently chosen from H, linear or branched $(C_1-C_6)$alkyl, cycloalkyl, aryl, aromatic or non aromatic heterocycle, linear or branched —$(C_1-C_6)$alkyl-aryl or linear or branched —$(C_1-C_6)$alkyl-heterocycle, wherein the heterocycle is aromatic or non aromatic; optionally substituted or not by OH, $CO_2H$, C(O)$NH_2$, $NH_2$ or their pharmaceutically acceptable salts or their optical isomers, racemates, diastereoisomers, enantiomers or tautomers.

The formula (I) of the invention refers to any of the following embodiments or any of their combinations.

Preferably, in compound of formula (I), $R^1$, each identical or different, is chosen from the group consisting of linear or branched $(C_1-C_6)$alkyl, halogen, OR, NRR', CN, $CF_3$, C(O)R, C(O)OR, C(O)NRR'; $NO_2$; $(C_1-C_6)$alkylene-OR, $(C_1-C_6)$alkylene-NRR', $(C_1-C_6)$alkylene-$CO_2$R, $(C_1-C_6)$alkylene-C(O)NRR', —O—$(C_1-C_6)$alkylene-$CO_2$R, —O—$(C_1-C_6)$alkylene-C(O)NRR', $CO_2$—$(C_1-C_6)$alkylene-OR, $CO_2$—$(C_1-C_6)$alkylene-NRR', C(O)NH—$(C_1-C_6)$alkylene-OR, C(O)NH—$(C_1-C_6)$alkylene-NRR' or NHC(O)R.

Preferably, in compound of formula (I), $L^1$ is linear or branched $(C_1-C_6)$alkylene optionally substituted by one or more of =O, CN, C(O)R, C(O)OR, or C(O)NRR'; or linear or branched $CH_2(C_1-C_6)$alkylene, wherein the later $(C_1-C_6)$alkylene is optionally substituted by one or more of halogen, OR, NRR' or $CF_3$.

Preferably, in compound of formula (I), $R^2$ is a linear or branched $(C_1-C_6)$alkylene and is linked together with $R^5$=linear or branched $(C_1-C_6)$alkylene to form with —X—$(CR^3R^4)_n$—N—, to which they are attached, an heterocycle of 5 or 6 members optionally substituted by one or more of OR, linear or branched $(C_1-C_6)$alkyl, halogen, NRR', CN, $CF_3$, C(O)R, C(O)OR, C(O)NRR', or =O.

Preferably, in compound of formula (I), $R^7$ is OR, $OR^9$, halogen, linear or branched $(C_1-C_6)$alkyl-OR, C(O)OR, C(O)NRR' or CN. More preferably $R^7$ is OR, $OR^9$. More preferably $R^7$ is OH or $OR^9$, preferably OH.

$R^6$ is chosen from the group consisting in aryl, heteroaryl, cycloalkyl, heterocycle, H, wherein the aryl, heteroaryl, cycloalkyl or heterocycle is mono or polycyclic and is optionally substituted by one or more of linear or branched $(C_1-C_6)$alkyl, halogen, NRR', CN, $CF_3$, OR, C(O)R, C(O)OR, NHC(O)R, OC(O)R or C(O)NRR'.

Preferably, in compound of formula (I), A is chosen from the group consisting of:
—C(O)—;
—C(O)NH—;
—$SO_2$—; or
—$SO_2$N—.

Preferably, in compound of formula (I), $L^2$ is linear or branched $(C_1-C_6)$alkylene optionally interrupted by at least one heteroatom chosen from O, NR or S and/or optionally substituted by: R, OR, NRR', $(C_1-C_6)$alkyl-OR, $(C_1-C_6)$alkyl-NRR', OC(O)R, NHC(O)R, NHC(O)NRR', CN, C(=NH)NHOR.

Preferably, it should be understood that $L_2$ does not represent O—$(C_1-C_6)$alkylene.

Preferably, in compound of formula (I):
$NR^5$ is directly bonded to at least one of C(O), C(O)N, $SO_2$ or $SO_2$N groups; and/or
i=0, n is 1, 2 or 3 and the $CR^3R^4$ linked to $NR^5$ is C(O); or i=1, A is —C(O)—, C(O)NH, $SO_2$ or $SO_2$N; and/or i=0, n is 1, 2 or 3 and the $CR^3R^4$ linked to $NR^5$ is C(O); or i=1, A is —C(O)—, C(O)NH, $SO_2$ or $SO_2N$, X is $CR^2R^7$ or $NR^2$ and $R^2$ and $R^5$, identical or different, are linear or branched ($C_1$-$C_6$)alkylene and form together with —X—$(CR^3R^4)_n$—N—, to which they are attached, an heterocycle of 5 to 7 members optionally substituted by one or more of OR, linear or branched ($C_1$-$C_6$)alkyl, halogen, NRR', CN, $CF_3$, C(O)R, C(O)OR, C(O)NRR' and $R^3$, $R^4$, each identical or different, are chosen in the group consisting of H, linear or branched ($C_1$-$C_6$)alkyl, halogen, OR, NRR', CN, $CF_3$, C(O)R, C(O)OR, C(O)NRR'; and/or i=1 and A is —C(O)—, X is $CR^2R^7$ or $NR^2$ and $R^2$ and $R^5$, identical or different, are linear or branched ($C_1$-$C_6$) alkylene and form together with —X—$(CR^3R^4)_n$—N—, to which they are attached, an heterocycle of 5 to 7 members optionally substituted by one or more of OR, linear or branched ($C_1$-$C_6$)alkyl, halogen, NRR', CN, $CF_3$, C(O)R, C(O)OR, C(O)NRR' and $R^3$, $R^4$, each identical or different, are chosen in the group consisting of H, linear or branched ($C_1$-$C_6$)alkyl, halogen, OR, NRR', CN, $CF_3$, C(O)R, C(O)OR, C(O)NRR'; and/or $R^1$, each identical or different, is chosen from the group consisting of linear or branched ($C_1$-$C_6$)alkyl, halogen, OR, NRR', CN, $CF_3$, C(O)R, C(O)OR, C(O)NRR', or NHC(O)R; and/or $R^1$, each identical or different, is chosen from the group consisting of linear or branched $C_1$-$C_6$(alkyl), halogen, OH or linear or branched —O—($C_1$-$C_6$)alkyl; and or $R^1$, each identical or different, is chosen from the group consisting of halogen or linear or branched —O—($C_1$-$C_6$)alkyl; and/or q is 0, 1 or 2; and/or X is $CR^2R^7$ or $NR^2$ and $R^2$ and $R^5$, identical or different, are linear or branched ($C_1$-$C_6$)alkylene and form together with —X—$(CR^3R^4)_n$—N—, to which they are attached, an heterocycle of 5 to 7 members optionally substituted by one or more of OR, linear or branched ($C_1$-$C_6$)alkyl, halogen, NRR', CN, $CF_3$, C(O)R, C(O) OR, or C(O)NRR'. Preferably, the heterocycle formed by —$XR^2$—$(CR^3R^4)_n$—$NR^5$— is a non aromatic heterocycle; and/or $R^3$, $R^4$, each identical or different, are chosen in the group consisting of H, linear or branched ($C_1$-$C_6$)alkyl, halogen, =O, OR, NRR', CN, $CF_3$, C(O)R, C(O)OR or C(O)NRR'; and/or $R^3$, $R^4$, each identical or different, are chosen in the group consisting of H, —O—($C_1$-$C_6$)alkyl, OH and =O. Preferably, $R^3$, $R^4$, each identical or different, are chosen in the group consisting of H and OH; and/or X is $CR^2R^7$, or aryl and $R^7$ is OR, $OR^9$, linear or branched ($C_1$-$C_6$)alkyl-OR, halogen, C(O)OH, NRR', C(O)$NH_2$ or SR. Preferably, X is $CR^2R^7$, or aryl and $R^7$ is OR, $OR^9$, NRR' or SR. More preferably, $R^7$ is OH or $OR^9$, preferably OH. $R^9$ being as defined above; and/or X is an aryl, preferably phenyl and/or $L^1$ is linear or branched $C_1$-$C_6$(alkylene) optionally substituted by one or more =O or is linear or branched $CH_2$—$C_1$-$C_6$(alkylene), wherein the later alkylene is optionally substituted by one or more OH; and/or $L^2$ is linear or branched $C_1$-$C_6$(alkylene)-O or linear or branched $C_1$-$C_6$(alkylene) optionally interrupted by at least one heteroatom chosen from O or S and/or optionally substituted by one or more of: R, OR, NRR', ($C_1$-$C_6$)alkyl-OR, ($C_1$-$C_6$)alkyl-NRR', OC(O)R, NHC(O)R, NHC(O)NRR', CN, C(=NH)NHOR. More preferably $L^2$ is linear or branched $C_1$-$C_6$(alkylene) or linear or branched —[$C_1$-$C_6$(alkylene)]—O—; and/or $R^6$ is chosen from the group consisting in aryl, heteroaryl, cycloalkyl or H, wherein the aryl, heteroaryl or cycloalkyl is optionally substituted by halogen, linear or branched O—($C_1$-$C_6$)alkyl; and/or $R^6$ is chosen from the group consisting in phenyl, thiophenyl, cyclopentyl and H, wherein the phenyl is optionally substituted by halogen, linear or branched O—($C_1$-$C_6$)alkyl.

In one embodiment, in the compound of formula (I), X is $CR^2R^7$ or $NR^2$ and $R^2$ and $R^5$ form together with X—$(CR^3R^4)_n$—N— to which they are attached an heterocycle of 5 to 7 members optionally substituted by one or more OH. Preferably, in this particular embodiment, n is 0, 1 or 2 and/or X is $CR^2R^7$ wherein $R^7$ is OR, $OR^9$, linear or branched ($C_1$-$C_6$)alkyl-OR, halogen, C(O)OH, C(O)$NH_2$, NRR' or SR, and/or $L^1$ is $(CH_2)_k$, wherein k is 1 or 2, preferably k is 1, —C(O)—, —$CH_2$—CH(OH)— or —$CH_2$—C(O)—. Preferably $R^7$ is OR, $OR^9$, NRR' or SR. More preferably, $R^7$ is OH or $OR^9$, preferably OH. $R^9$ being as defined above.

In another embodiment, in the compound of formula (I), X is aryl, heteroaryl, cycloalkyl or heterocycle, wherein the aryl, heteroaryl, cycloalkyl or heterocycle is optionally substituted by one or more of linear or branched $C_1$-$C_6$ (alkyl), halogen, OR, NRR', CN, $CF_3$, C(O)R, C(O)OR or C(O)NRR', preferably X is aryl and $R^5$ is H or linear or branched $C_1$-$C_6$(alkyl), preferably H. Preferably, in this particular embodiment, n is 0 and/or X is aryl and/or $L^1$ is —$CH_2$—CH(OH)—.

DETAILED DESCRIPTION OF THE PREFERRED EMBODIMENTS

According to a particular embodiment, compounds of the invention may be of the following formula (Ia)

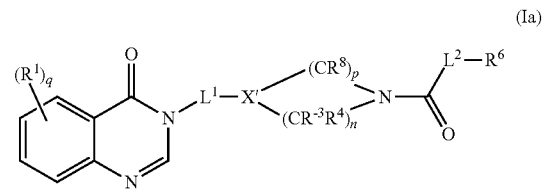

wherein
$R^1$, q, $L^1$, $L^2$, $R^6$ and $R^7$ are as defined in formula (I);
X' is $CR^7$ or N;
n is 0, 1 or 2;
p is 1, 2 or 3;
$R^3$, $R^4$ and $R^8$, each identical or different, are chosen in the group consisting of H, linear or branched ($C_1$-$C_6$)alkyl, halogen, OH, —O—($C_1$-$C_6$)alkyl, NRR', CN, $CF_3$, OR, C(O)R, C(O)OR or C(O)NRR'.

Preferably in the compound of formula (Ia), $R^3$, $R^4$ and $R^8$, each identical or different, are chosen in the group consisting of H or OH; and/or p is 1 or 2.

Preferably in compound of formula (Ia)

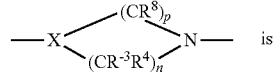 is

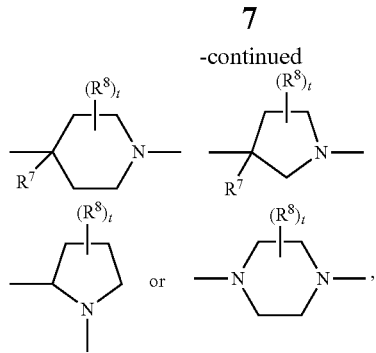

t is 0, 1 or 2 preferably

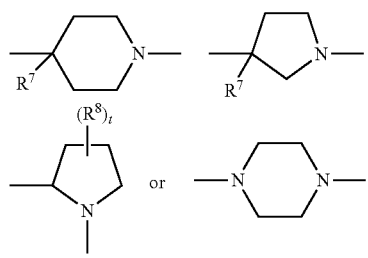

wherein R$^7$ is OR, halogen, linear or branched (C$_1$-C$_6$) alkyl-OR, C(O)OR, C(O)NRR', CN, OR$^9$, NRR' or SR, more preferably OR, OR$^9$, NRR' or SR, preferably OH or OR$^9$, p is 1 or 2 and R$^8$ is chosen in the group consisting of H or OH.

According to a particular embodiment, compounds of the invention may be of the following formula (Ia)

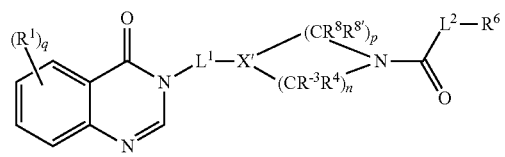

(Ia)

wherein

R$^1$, q, L$^1$, L$^2$, R$^6$ and R$^7$ are as defined in formula (I);

X' is CR$^7$ or N;

n is 0, 1 or 2;

p is 1, 2 or 3;

R$^3$, R$^4$, R$^8$ and R$^{8'}$, each identical or different, are chosen in the group consisting of H, linear or branched (C$_1$-C$_6$)alkyl, halogen, OH, —O—(C$_1$-C$_6$)alkyl, NRR', CN, CF$_3$, OR, C(O)R, C(O)OR or C(O)NRR'.

Preferably in the compound of formula (Ia), R$^3$, R$^4$, R$^8$ and R$^{8'}$, each identical or different, are chosen in the group consisting of H or OH; and/or p is 1 or 2.

Preferably in compound of formula (Ia)

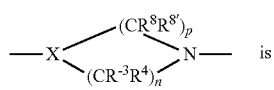 is

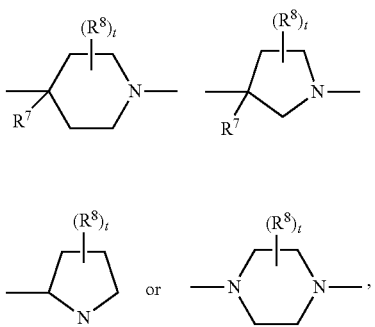

is 0, 1 or 2 preferably

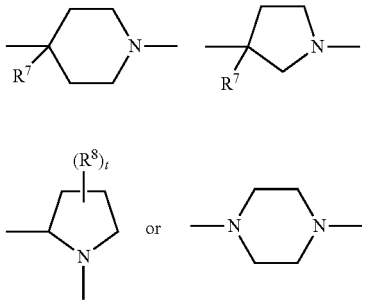

wherein R$^7$ is OR, halogen, linear or branched (C$_1$-C$_6$) alkyl-OR, C(O)OR, C(O)NRR', CN, OR$^9$, NRR' or SR, more preferably OR, OR$^9$, NRR' or SR, preferably OH or OR$^9$, p is 1 or 2 and R$^8$ is chosen in the group consisting of H or OH.

According to a particular embodiment, compounds of the invention may be of the following formula (Ib)

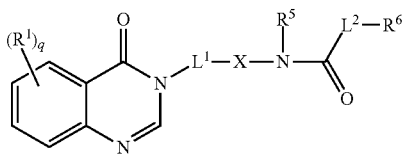

(Ib)

wherein

R$^1$, q, L$^2$ and R$^6$ are as defined for compounds of formula (I);

X is aryl, heteroaryl, cycloalkyl or heterocycle, wherein the aryl, heteroaryl, cycloalkyl or heterocycle is optionally substituted by one or more of linear or branched C$_1$-C$_6$(alkyl), halogen, OH, linear or branched —O—(C$_1$-C$_6$)alkyl, NRR', CN, CF$_3$, OR, C(O)R, C(O)OR or C(O)NRR';

R$^5$ is H or linear or branched (C$_1$-C$_6$)alkyl;

L$^1$ is linear or branched (C$_1$-C$_6$)alkyl substituted by one or more OH.

Preferably in compound of formula (Ib), X is phenyl.

Preferably in compound of formula (Ib), R$^5$ is H.

According to a particular embodiment, compounds of the invention may be of the following formula (I')

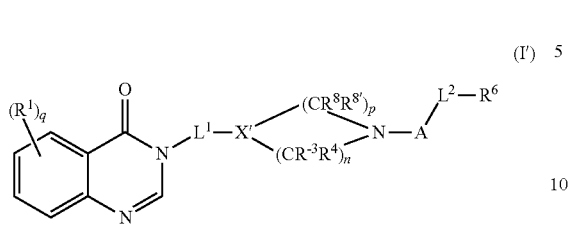
(I')

wherein
$R^1$, q, $L^1$, A, $L^2$, R, R' and $R^6$ are as defined in formula (I);
X' is $CR^7$;
$R^7$ is OR, halogen, linear or branched ($C_1$-$C_6$)alkyl-OR, C(O)OR, C(O)NRR', CN,
$OR^9$, NRR' or SR, more preferably OR, $OR^9$, NRR' or SR;
$R^9$ is as defined in formula (I);
n is 0, 1 or 2;
p is 1, 2 or 3;
$R^3$, $R^4$, $R^8$ and $R^{8'}$, each identical or different, are chosen in the group consisting of H, linear or branched ($C_1$-$C_6$)alkyl, halogen, OH, —O—($C_1$-$C_6$)alkyl, NRR', CN, $CF_3$, OR, C(O)R, C(O)OR or C(O)NRR'.

Preferably, in compound of formula (I), A is chosen from the group consisting of:
—C(O)—;
—C(O)NH—;
—$SO_2$—; or
—$SO_2$N—.

Preferably, in the compounds of formula (I'), $R^3$, $R^4$, $R^8$ and $R^{8'}$, each identical or different, are chosen in the group consisting of H or OH, and/or p is 1 or 2.

Preferably, in the compounds of formula (I') $R^7$ is OR, halogen, linear or branched ($C_1$-$C_6$)alkyl-OR, C(O)OR, C(O)NRR', CN, more preferably OH.

Preferably, in the compounds of formula (I') $R^7$ is OR, $OR^9$, NRR' or SR, more preferably $R^7$ is OR, $OR^9$, preferably OH or $OR^9$, for example OH.

Preferably, in the compounds of formula (I') p+n=4; more preferably p is 2 and n is 2.

Preferably in compound of formula (I')

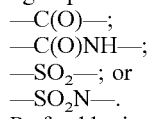 is 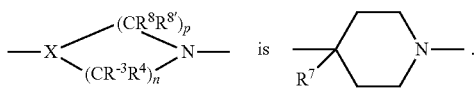

Preferably, in the compounds of formula (I') $L^1$ is $CH_2$.
Preferably, in the compounds of formula (I') p is 2 and n is 2, $R^7$ is OR, $OR^9$, NRR' or SR, more preferably $R^7$ is OR, $OR^9$, preferably OH or $OR^9$, for example OH.
Preferably, in the of formula (I') p is 2 and n is 2, and $L^1$ is $CH_2$.
Preferably, in the compounds of formula (I') $L^1$ is $CH_2$ and $R^7$ is OR, $OR^9$, NRR' or SR, more preferably $R^7$ is OR, $OR^9$, preferably OH or $OR^9$, for example OH.
Preferably, in the compounds of formula (I') p is 2 and n is 2, $L^1$ is $CH_2$, $R^7$ is $R^7$ is OR, $OR^9$, NRR' or SR, more preferably $R^7$ is OR, $OR^9$, preferably OH or $OR^9$, for example OH.

According to a particular embodiment, in the compounds of formula (I') A is C═O, the compound is thus of the following formula (Ia')

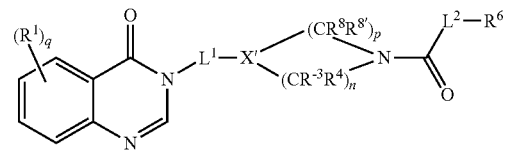
(Ia')

wherein $R^1$, q, n, p, X', $R^3$, $R^4$, $R^8$, $R^{8'}$, $L^2$, $R^6$ and $R^7$ are as defined in formula (I').

Preferably in compound of formula (Ia')

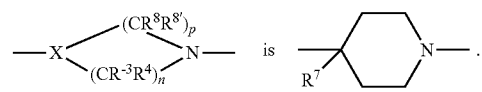 is 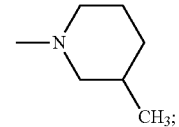.

According to a specific embodiment, the invention relates to compounds of formula (I) as defined above with the exception of the following compound:
q is 0, $L^1$ is $CH_2$, X—$(CR^3R^4)_n$—$NR^5$ forms a piperidine, X is $CR^2R^7$ and $R^7$ is OH, i is 1, A is C═O, $L^2$ is $C_2H_4$ and $R^6$ is

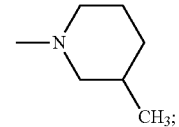

q is 1, $R^1$ is Cl at position 7, $L^1$ is $CH_2$, X—$(CR^3R^4)_n$—$NR^6$ forms a piperidine, X is $CR^2R^7$ and $R^7$ is OH, i is 1, A is C═O, $L^2R^6$ is $CH(CH_2CH_3)_2$.

According to a specific embodiment, the compounds of formula (I) are chosen from:
3-({4-hydroxy-1-[3-(2-methoxyphenyl)propanoyl]piperidin-4-yl}methyl)-3,4-dihydroquinazolin-4-one
7-chloro-3-{[1-(2-ethylbutanoyl)-4-hydroxypiperidin-4-yl]methyl}-3,4-dihydroquinazolin-4-one
3-({1-[2-(3-fluorophenoxy)acetyl]-4-hydroxypiperidin-4-yl}methyl)-3,4-dihydroquinazolin-4-one
3-{[4-hydroxy-1-(2-methylpropanoyl)piperidin-4-yl]methyl}-6,7-dimethoxy-3,4-dihydroquinazolin-4-one
3-{[4-hydroxy-1-(2-methylpropanoyl)piperidin-4-yl]methyl}-3,4-dihydroquinazolin-4-one 4-hydroxy-1-[2-methyl-3-(thiophen-2-yl)propanoyl]piperidin-4-yl}methyl)-3,4-dihydroquinazolin-4-one
7-chloro-3-{[1-(3-cyclopentylpropanoyl)-4-hydroxypiperidin-4-yl]methyl}-3,4-dihydroquinazolin-4-one
3-{[1-(3-cyclopentylpropanoyl)-4-hydroxypiperidin-4-yl]methyl}-3,4-dihydroquinazolin-4-one
7-chloro-3-{[4-hydroxy-1-(3-phenylpropanoyl)piperidin-4-yl]methyl}-3,4-dihydroquinazolin-4-one
3-{[4-hydroxy-1-(3-phenylpropanoyl)piperidin-4-yl]methyl}-3,4-dihydroquinazolin-4-one
7-chloro-3-({4-hydroxy-1-[2-methyl-3-(thiophen-211)propanoyl]piperidin-4-yl}methyl)-3,4-dihydroquinazolin-4-one
3-({4-hydroxy-1-[3-(thiophen-2-yl)propanoyl]piperidin-4-yl}methyl)-3,4-dihydroquinazolin-4-one
3-{[1-(2-benzylpropanoyl)-4-hydroxypiperidin-4-yl]methyl}-3,4-dihydroquinazolin-4-one 3-{[1-(2-benzylpropanoyl)-4-hydroxypiperidin-4-yl]
methyl}-7-chloro-3,4-dihydroquinazolin-4-one,
or their pharmaceutically acceptable salts or their optical isomers, racemates, diastereoisomers, enantiomers or tautomers.

As used hereabove or hereafter:

"Alkyl" means an aliphatic hydrocarbon group which may be straight or branched having 1 to 6 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl.

As used herein, the term "cycloalkyl" refers a non aromatic monocyclic or multicyclic hydrocarbon ring of 3 to 10 carbon atoms formed by the removal of one hydrogen atom. A designation such as "$C_5$-$C_7$ cycloalkyl" refers to a cycloalkyl radical containing from 5 to 7 carbon atoms. Examples include cyclopropyl, cyclobutyl, cyclopentyl, cyclohexyl, cycloheptyl, adamantyl, etc. as well as the systems formed by their condensation or by the condensation with a phenyl group.

"Alken" or alkenyl means an aliphatic hydrocarbon group containing a carbon-carbon double bond and which may be straight or branched having 2 to 6 carbon atoms in the chain. Preferred alkenyl groups have 2 to 6 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl.

"Halogen atom" refers to fluorine, chlorine, bromine or iodine atom; preferably fluorine and chlorine atom.

"Aryl" means an aromatic monocyclic or multicyclic hydrocarbon ring system of 6 to 14 carbon atoms, preferably of 6 to 10 carbon atoms, substituted or not. Exemplary aryl groups include phenyl or naphthyl.

As used herein, the terms "heterocycle" or "heterocyclic" refer to a saturated, partially unsaturated or unsaturated, non aromatic stable 3 to 14, preferably 5 to 10-membered mono, bi or multicyclic rings wherein at least one member of the ring is a hetero atom, substituted or not. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics*, 76$^{th}$ Edition, CRC Press, Inc., 1995-1996, p. 2-25 to 2-26, the disclosure of which is hereby incorporated by reference. Example of aromatic heterocycle is thiophenyl.

Preferred non aromatic heterocyclic include, but are not limited to pyrrolidinyl, pyrazolidinyl, imidazolidinyl, oxiranyl, tetrahydrofuranyl, dioxolanyl, tetrahydro-pyranyl, dioxanyl, dioxolanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydropyridyl, dihydropyridyl, tetrahydropyrinidinyl, dihydrothiopyranyl, azepanyl, as well as the fused systems resulting from the condensation with a phenyl group, each substituted or not.

As used herein, the term "heteroaryl" or aromatic heterocycles refers to a 5 to 14, preferably 5 to 10-membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "cycloalkyl", "aryl", "heteroaryl", "heterocycle" and the likes refers also to the corresponding "alkylene", "cycloalkylene", "arylene", "heteroarylene", "heterocyclene" and the likes which are formed by the removal of two hydrogen atoms. Alkyl and alkylene are used herein interchangeably.

As used herein, the term "patient" refers to either an animal, such as a valuable animal for breeding, company or preservation purposes, or preferably a human or a human child, which is afflicted with, or has the potential to be afflicted with one or more diseases and conditions described herein.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

As used herein, the expression "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like, including mono, di or tri-salts thereof; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 20$^{th}$ ed., Mack Publishing Company, Easton, Pa., 2000, the disclosure of which is hereby incorporated by reference.

The compounds of the general formula (I) having geometrical and stereoisomers are also a part of the invention.

According to a further object, the present invention is also concerned with the process of preparation of the compounds of formula (I).

The compounds and process of the present invention may be prepared in a number of ways well-known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, Wiley-VCH Publishers, 1999.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxyl, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, 4th ed. (2007), John Wiley & Sons Inc., 1999; J. F. W. McOmie in *Protective Groups in Organic Chemistry*, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, benzene, toluene and xylene; amides, such as dimethylformamide; alcohols such as ethanol and methanol and ethers, such as diethyl ether and tetrahydrofuran.

The reactions can take place over a wide range of temperatures. In general, it is found convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a water-immiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is a further object of the present invention.

According to a first aspect, a compound of the invention of formula (I) can be obtained by reacting a compound of formula (II) with a compound of formula (III) in order to form secondary or tertiary amines, carboxamides, urea, sulfonamides or thioureas,

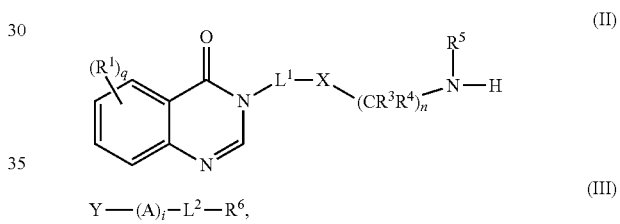

$$Y-(A)_i-L^2-R^6, \quad (III)$$

wherein $R^1$, $R^3$, $R^4$, $R^5$, $R^6$, $L^1$, $L^2$, X, A, q, n et i are defined as above for formula (I), Y is a leaving group.

The leaving group is such that reactive functions of compounds (II) and (III) lead to the —$NR^5$-(A)i-group as in formula (I).

Preferably, the leaving group Y is chosen from halogen, OH, activated OH such as a group of R—S(O)$_2$O—, wherein R is an aryl or a linear or branched $C_1$-$C_6$(alkyl). Preferably, R—S(O)$_2$O— is a Ts- or Ms-group with Ts is

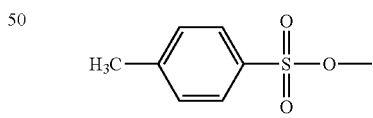

and Ms is

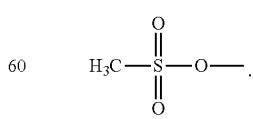

More specifically, when the group consisting of —NR$_5$-(A)i- in compounds (I) is:

Secondary or Tertiary amines: Y is a leaving group chosen from halogen, OH, activated OH such as a group of R—S(O)$_2$O—, wherein R is an aryl or a linear or branched C$_1$-C$_6$(alkyl). Preferably, R—S(O)$_2$O— is a Ts- or Ms- group with Ts is

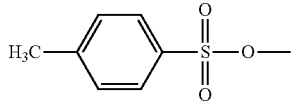

and Ms is

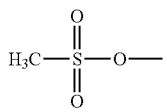

and i=0. Generally, these reactions are alkylations, Mitsunobu reactions and are performed according methods well known in the art; or Carboxamides: Y and A form an acid chloride or a carboxylic acid. Generally, when Y is OH, i is 1 and A is C(O), peptidic coupling reaction conditions are used;

Generally, when Y is OH, i is 1 and A is C(O) this reaction is carried out in the presence of coupling reagents such as EDCl (1-ethyl-3-[3-(dimethylamino)propyl]carbodiimide hydrochloride) and HOBt (N-hydroxybenzotriazol), with or without a base (e.g. Et$_3$N) in an aprotic solvent such as dichloromethane or dimethylformamide;

or

Ureas: Y and A form an isocyanate; or

Sulfonamides: Y and A form a sulfonyl chloride; or

Thioureas: Y and A form a thioisocyanate.

Preferably, the compound of formula (II) is a compound of formula (IIa)

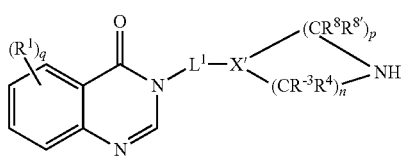

(IIa)

wherein R$^1$, q, L$^1$, X', R$^8$, R$^{8'}$, p, R$^3$, R$^4$ et n are as defined for formula (I') and (Ia).

According to a second aspect, a compound of the invention of formula (I) can be obtained by reacting a compound of formula (IV) with a compound of formula (V)

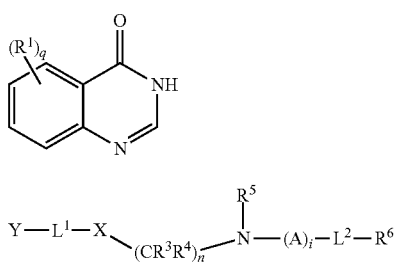

wherein R$^1$, R$^3$, R$^4$, R$^5$, R$^6$, L$^1$, L$^2$, X, q, n et i are defined above and Y is a leaving group. Preferably, Y is chosen from epoxy, halogen, activated OH as defined above.

More preferably the compound of formula (V) is a compound of formula (Va)

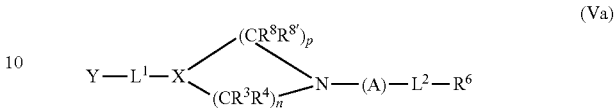

(Va)

wherein, X, R$^8$, R$^{8'}$, p, R$^3$, R$^4$, n, A, L$^2$ and R$^6$ are as defined for formula (I') and (Ia).

This reaction is generally carried out in presence of a base, preferably an inorganic base and in a solvent, preferably a polar aprotic solvent.

The compounds of formula (III) and (IV) are commercially available or can be prepared by the person skilled in the art based on its general knowledge in organic chemistry.

The compounds of formula (II) and (V) are obtained as described in the general procedure below.

According to a third aspect, a compound of the invention of formula (I) can be obtained by reacting a corresponding compound of formula (Ic)

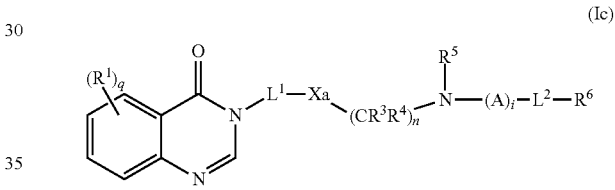

(Ic)

Wherein, R$^1$, R$^2$, R$^3$, R$^4$, R$^5$, R$^6$, L$^1$, L$^2$, q, n and i are as defined for formula (I) and Xa is a precursor group of X. The compound of formula (Ic) may be obtained from corresponding compounds of formula (IIc) and (IIIc) or (IVc) and (Vc), respectively, by analogy with compounds of formula (I) as above.

The term "precursor" is used herein to refer to compounds which differ from the indicated or desired compounds by the presence and/or absence of groups or functions. Such groups or functions may be introduced, transformed and/or omitted by common functionalization reactions, known from the skilled person.

The functionalization reaction may be carried out by application or adaptation of known methods.

Preferably, the precursor group is such that it enables by one ore more step to obtain X starting from Xa, such as for example by reduction, amidification, oxidation, hydrolysis, esterification.

The above reactions can be carried out by the skilled person by applying or adapting the methods illustrated in the examples hereinafter.

Further, the process of the invention may also comprise the additional step of isolating the compound of formula (I), (I'), (Ia), (Ib) or (I'a). This can be done by the skilled person by any of the known conventional means, such as the recovery methods described above.

Generally, the starting products are commercially available mainly from Aldrich or Acros or other typical chemicals supplier or may be obtained by applying or adapting any known methods or those described in the examples.

According to a further object, the present invention concerns also the pharmaceutical compositions comprising a compound of formula (I), (I'), (Ia), (Ib) or (I'a) as defined above with a pharmaceutically acceptable excipient.

Preferred embodiments of formula (I), (I'), (Ia), (Ib) or (I'a) are as defined above in respect of the compounds of the invention and according to anyone of the preferred features or embodiment.

According to a still further object, the present invention concerns a compound of formula (I) of the invention for inhibiting cysteine protease.

Advantageously, the compounds of formula (I), (I'), (Ia), (Ib) or (I'a) enables a selective and reversible inhibition of cysteine protease.

The compounds and the pharmaceutical composition of the invention are useful for inhibiting cysteine proteases, in particular specific de-ubiquitination enzymes such as USPs, and more particularly USP-7 in patients in the need thereof.

The compounds and the pharmaceutical composition of the invention are particularly useful for treating and/or preventing cancer and metastasis, more particularly prostate and/or colon cancers, neurodegenerative diseases, such as Alzheimer's disease and Parkinson's disease, immunological disorders, bone and joint diseases, osteoporosis, arthritis inflammatory disorders, cardiovascular diseases, viral infections and diseases, and/or viral infectivity and/or latency, bacterial infections and diseases.

The compound and pharmaceutical composition of the invention can be used on patients which do not have beta-amyloïd plaques that act on senile dementia especially, Alzheimer's disease.

In particular, said viral infections and diseases are chosen from herpes simplex-1 or -2 viral infections, hepatitis A, hepatitis C, SARS coronavirus infection and disease, Epstein-Barr virus, rhinoviral infections and diseases, adenoviral infections and diseases, poliomyelitis.

According to an aspect, said compounds inhibit one or more viral cysteine proteases.

Bacterial cysteine proteases may be chosen from streptopain, clostripain, staphylococcal cysteine protease, gingipain.

The present invention also concerns the combinations comprising a compound of formula (I) as defined above with one or more active agents chosen from anti-cancer agents, neurological agents, thrombolytic agents, antioxidant agents, anti-infective, antihypertensive agents, diuretic agents, thrombolytic agents, immunosuppressive agents, cardiovascular agents, immunomodulatory agents, anti-inflammatory agents, antiviral agents, anti-bacterial agents.

The present invention also concerns the corresponding methods of treatment comprising the administration of a compound of the invention together with a pharmaceutically acceptable carrier or excipient to a patient in the need thereof.

According to the invention, the terms "patient" or "patient in need thereof", are intended for an animal or a human being affected or likely to be affected with a pathological condition involving an active cysteine protease in its pathogenesis. Preferably, the patient is human.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

"Therapeutically effective amount" means an amount of a compound medicament according to the present invention effective in preventing or treating a pathological condition requiring the inhibition of an active cysteine protease involved in its pathogenesis.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), (I'), (Ia), (Ib) or (I'a), which is required to achieve the desired biological effect, will vary depending upon a number of factors, including the chemical characteristics (e.g. hydrophobicity) of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

In general terms, the compounds of this invention may be provided in an aqueous physiological buffer solution containing 0.1 to 10% wv compound for parenteral administration. Typical dose ranges are from 1 μg/kg to 0.1 g/kg of body weight per day; a preferred dose range is from 0.01 mg/kg to 100 mg/kg of body weight per day or an equivalent dose in a human child. The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compounds of the present invention are also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical total daily dose ranges are from 0.01 to 100 mg/kg of body weight. By way of general guidance, unit doses for humans range from 1 mg to 3000 mg per day. Preferably, the unit dose range is from 1 to 500 mg administered one to six times a day, and even more preferably from 10 mg to 500 mg, once a day. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well-known in the pharmaceutical art, for example, as described in Remington: The Science and Practice of Pharmacy, 20$^{th}$ ed.; Gennaro, A. R., Ed.; Lippincott Williams & Wilkins: Philadelphia, Pa., 2000.

Preferred formulations include pharmaceutical compositions in which a compound of the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactidegly-colide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

BRIEF DESCRIPTION OF THE DRAWING FIGURES

The invention is further illustrated but not restricted by the description in the following examples and figures as a non limiting illustration for selective inhibition of USP7 deubiquitinating activity over a panel of active DUBs in physiological conditions.

EXPERIMENTAL

Figure 1:
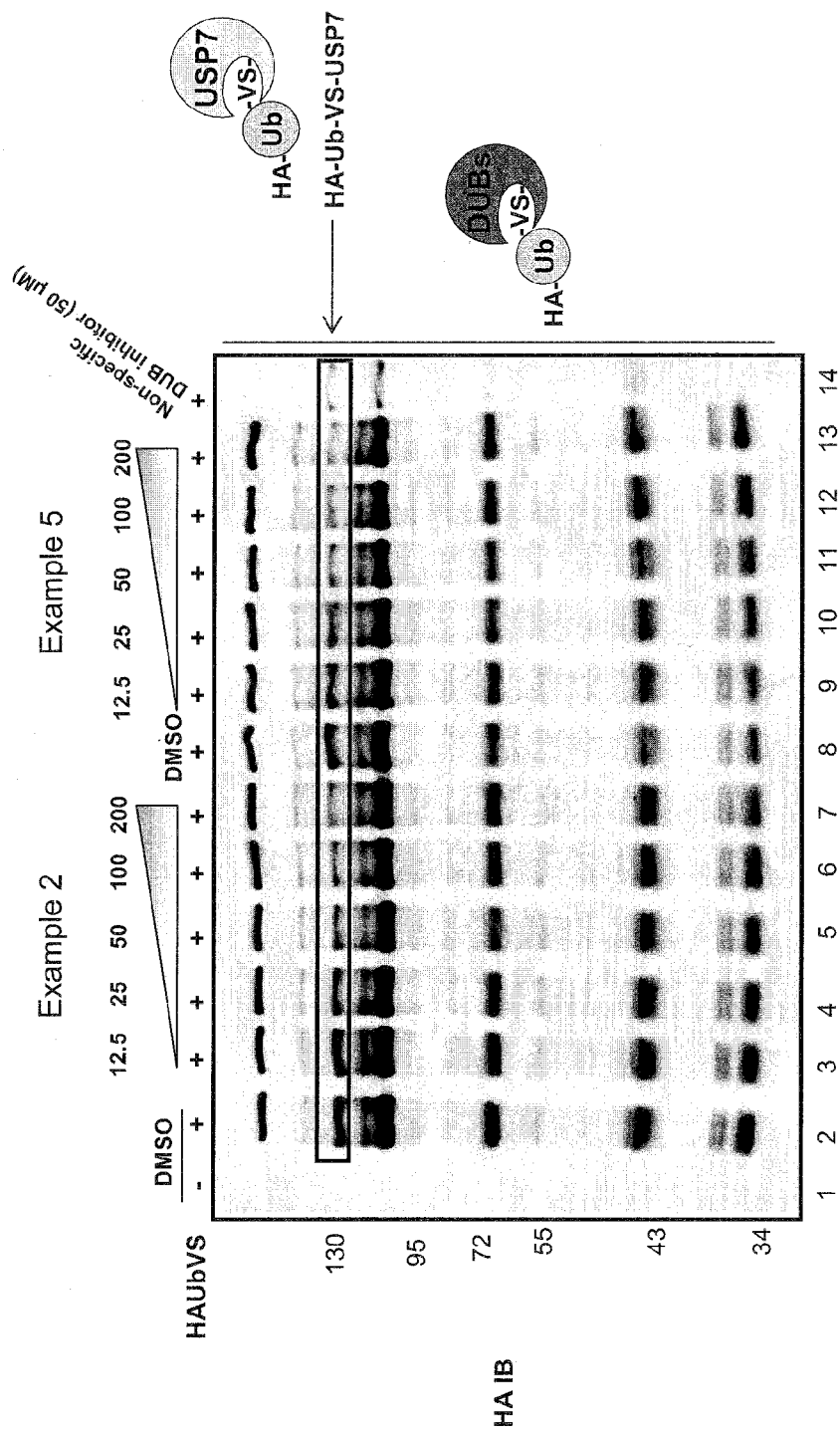
FIG. 1 shows a competitive HAUbVS gel for example 2 and example 5 (12.5-25-50-100-200 μM) using the HEK293 proteome.

Representative compounds of the invention are summarized in the table below:

| Formula | Example |
|---------|---------|
| ![structure 1] | 1 |
| ![structure 2] | 2 |

-continued

| Formula | Example |
|---------|---------|
| 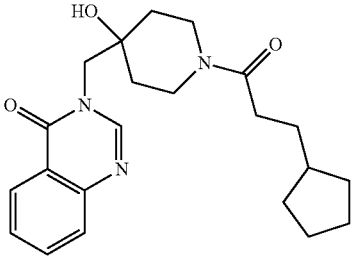 [SMILES: O=C(CCC1CCCC1)N1CCC(O)(Cn2cnc3ccccc3c2=O)CC1] | 3 |
| 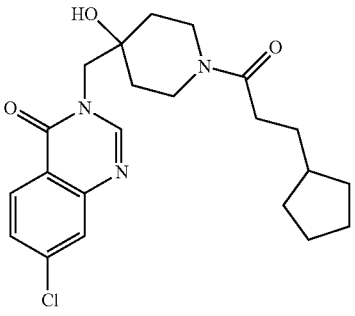 [SMILES: O=C(CCC1CCCC1)N1CCC(O)(Cn2cnc3cc(Cl)ccc3c2=O)CC1] | 4 |
| 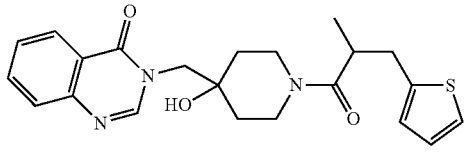 [SMILES: CC(Cc1cccs1)C(=O)N1CCC(O)(Cn2cnc3ccccc3c2=O)CC1] | 5 |
| 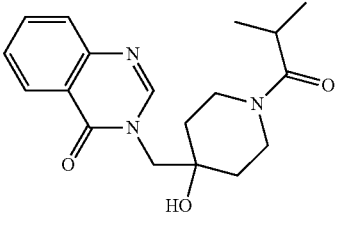 [SMILES: CC(C)C(=O)N1CCC(O)(Cn2cnc3ccccc3c2=O)CC1] | 6 |
| 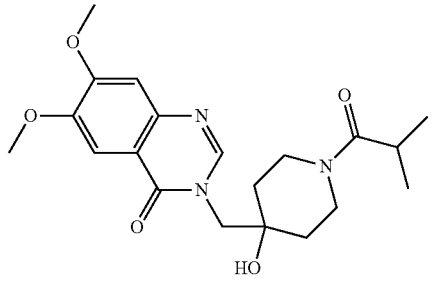 [SMILES: COc1cc2ncn(CC3(O)CCN(C(=O)C(C)C)CC3)c(=O)c2cc1OC] | 7 |
| 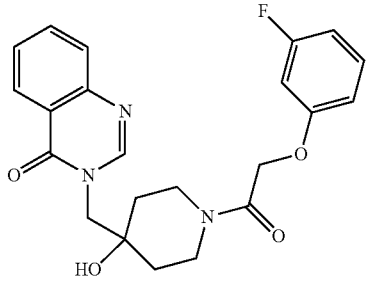 [SMILES: O=C(COc1cccc(F)c1)N1CCC(O)(Cn2cnc3ccccc3c2=O)CC1] | 8 |

-continued

| Formula | Example |
|---------|---------|
| 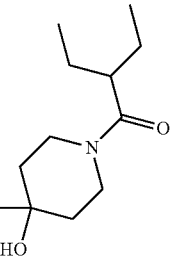 | 9 |
| 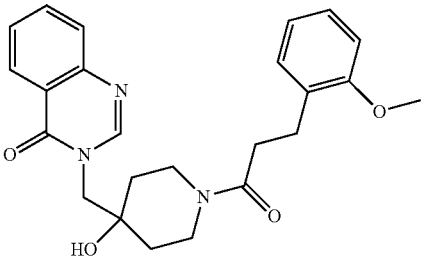 [SMILES: COc1ccccc1CCC(=O)N1CCC(O)(Cn2cnc3ccccc3c2=O)CC1] | 10 |
| 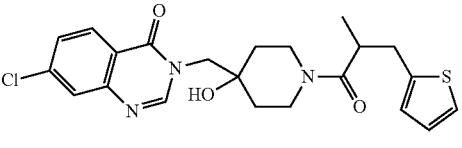 [SMILES: CC(Cc1cccs1)C(=O)N1CCC(O)(Cn2cnc3cc(Cl)ccc3c2=O)CC1] | 11 |
| 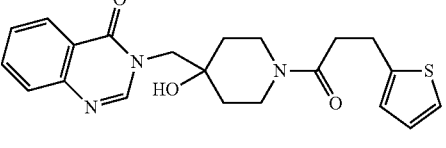 | 12 |
| 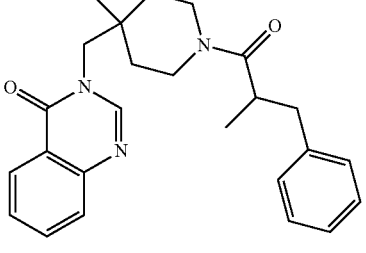 | 13 |
| 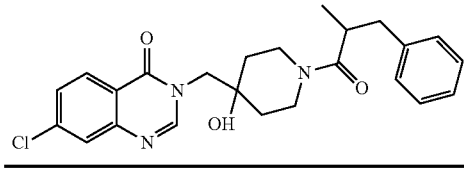 | 14 |

Representative compounds of the invention can be synthesized according to the following procedures.

General Analytical Procedures

NMR spectra were recorded at 300 or 400 MHz for $^1$H and at 75 or 100, MHz for $^{13}$C on a Bruker or Varian spectrometer with CDCl$_3$ or DMSO-d$_6$ (dimethyl sulfoxide) as solvent. The chemical shifts are given in ppm, referenced to the internal TMS (Trimethylsilyl) or deuterated solvent signal.

LC-MS analysis was used to analyze and purify target compounds. LC-MS analyses were performed using an Waters Micromass, Bruker Esquire 3000 (ESI-IT) or Agilent Iontrap XCT-Plus mass spectrometers and Waters Alliance 2790 or Agilent 1100 Series LC systems with UV and/or DAD detection. Columns: Waters XTerra MS C18, 30×2.1 mm (3.5 μm), Atlantis T3 C18, 3 μm, 50 mm×2.1 mm or Inertsil C8, 250 mm, 4.6 mm, 5 μm. Flow rates: 0.8-1.2 ml/min, Gradients: a) water 10% MeOH (methanol), ammonium formate 10 mM, to 100% MeOH or b) 95% Water-acetonitrile, 0.1% HCOOH to 95% acetonitrile.). UV detection: 190 to 400 nm. All compounds were >95% pure.

Representative Procedure 1

Preparation of Examples 1-14

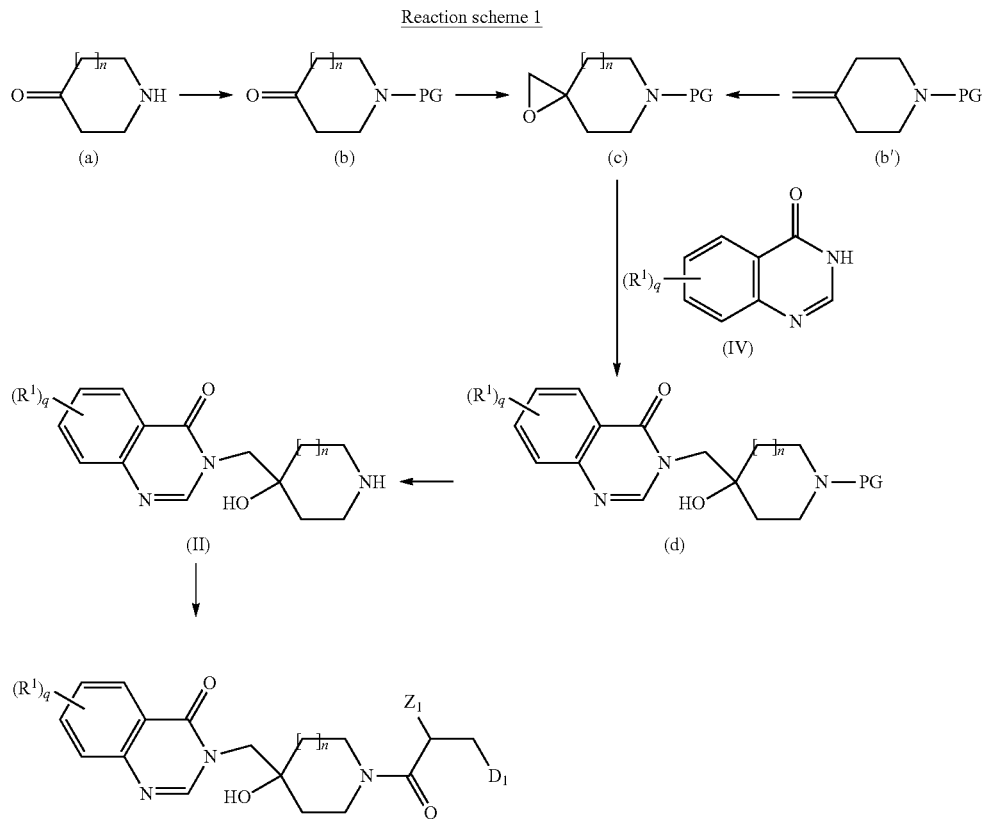

Reaction scheme 1

Compounds of formula (c) are obtained either from compound (b) via a Corey-Chaycovsky reaction as described in *J. Amer. Chem. Soc.* 1965, 87, 1353-1364 and WO2005054249 or either by epoxidation of the double bond of derivatives (b'). Compound (b) are commercially available or obtained from compound (a) after protection reactions well known in the art. The protecting group (PG) is for example benzyl (Bn), benzoyl (Bz), ter-butyloxycarbonyl (BOC) or Carbobenzyloxy (Cbz).

Oxirane (c) ring opening with quinazolinone (IV) is performed in the presence of a base like NaH, KF, $K_2CO_3$, $Cs_2CO_3$ when heating between 50 and 100° C. in dimethylformamide, acetone, etc. . . . .

Deprotection of the piperidine nitrogen is performed according to known methods gives compound (II).

Peptide coupling reaction are performed according to well known methods in the art between compound (II) and acid derivatives HO—C(O)—CH$_2$(Z$_1$)—CH$_2$-D (compound III). For some examples conditions like EDCl (1-ethyl-3-[3-(dimethylamino)propyl]carbodiimide hydrochloride), HOBt (N-hydroxybenzotriazol) and Et$_3$N in Dichloromethane (CHCl$_2$) were preferred. Amide bond formation is also possible when reacting with the acid chloride derivative.

Compounds (IV) are commercially available or prepared according to literature procedures The following compounds are obtained by the implementation of representative procedure 1:
q is 0, n is 1, Z1 is H and D1 is phenyl (example 1, described in the experimental part)
q is 1, n is 1, R1 is Cl, Z1 is H and D1 is phenyl (example 2)
q is 0, n is 1, Z1 is H and D1 is cyclopentyl (example 3)
q is 1, n is 1, R1 is Cl, Z1 is H and D1 is cyclopentyl (example 4)
q is 0, n is 1, Z1 is CH3 and D1 is thiophenyl (example 5)
q is 0, n is 1, Z1 is CH3 and D1 is H$_2$ (example 6)
q is 2, R1 is OMe, n is 1, Z1 is CH3 and D1 is H$_2$ (example 7)
q is 1, R1 is Cl, n is 1, Z1 is CH2CH3 and D1 is CH3 (example 9)
q is 0, n is 1, Z1 is H, D1 is 2-Ome-phenyl (example 10)
q is 1, R1 is Cl, n is 1, Z1 is CH3, D1 is thiophenyl (example 11)
q is 0, n is 1, Z1 is H, D1 is thiophenyl (example 12)
q is 0, n is 1, Z1 is CH3, D1 is phenyl (example 13)
q is 1, R1 is Cl, n is 1, Z1 is CH3 and D1 is phenyl (example 14)

Selected data of some of the compounds that were prepared by application or adaptation of the method disclosed above are shown below:

EXPERIMENTAL

Example 1

3-{[4-hydroxy-1-(3-phenylpropanoyl)piperidin-4-yl]methyl}-3,4-dihydroquinazolin-4-one Step 1: Preparation of tert-butyl 1-oxa-6-azaspiro[2.5]octane-6-carboxylate To a stirred solution of 1-Boc-4-piperidone (6.1 g, 30.6 mmol, 1 eq) in tetrahydrofuran (200 mL) was added trimethylsulfoxonium iodide (6.8 g, 30.6 mmol, 1 eq) and potassium tert-butoxide (4.0 g, 30.6 mmol, leg). The mixture was refluxed for 18 h and concentrated in vacuo. The crude product was dissolved in AcOEt (100 mL), and washed with water (100 mL). The layers were separated, and the aqueous layer was extracted with AcOEt. The combined organic extracts were dried over $Na_2SO_4$, filtered and concentrated in vacuo. The solid was purified by flash column chromatography on silica gel (eluent: cyclohexane/ethyl acetate 9/1) to give compound tert-butyl 1-oxa-6-azaspiro[2.5]octane-6-carboxylate (3.3 g, 52%) as a white solid.

Step 2: Preparation of tert-butyl 4-hydroxy-4-[(4-oxo-3,4-dihydroquinazolin-3-yl)methyl]piperidine-1-carboxylate To a solution of 4-hydroxyquinazoline (1.65 g, 11.3 mmol, 1.1 eq) in DMF (20 mL) was added compound from step 1 (2.35 g, 1 eq) and cesium carbonate (10.34 g, 3 eq). The mixture was heated at 80° C. overnight. The mixture was washed with a saturated solution of $NH_4Cl$, the aqueous layer was extracted with AcOEt. The organic extract was dried over $Na_2SO_4$, filtered and concentrated in vacuo. The crude product was purified by flash chromatography on silica gel (eluent: cyclohexane/ethyl acetate 3/7) to give tert-butyl 4-hydroxy-4-[(4-oxo-3,4-dihydroquinazolin-3-yl)methyl]piperidine-1-carboxylate (1.6 g, 40%) as a colourless oil.

MS (ES+, mz): 360.2 [M+H]+, 719.6 [2M+H]+

Step 3: Preparation of Trifluoroacetate salt of 3-[(4-hydroxypiperidin-4-yl)methyl]-3,4-dihydroquinazolin-4-one Compound from step 2 (1.0 g, 2.8 mmol) was dissolved in TFA (trifluoroacetic acid) (80 mL) and the reaction mixture was stirred at room temperature overnight. The resulting mixture was concentrated in vacuo. The crude Trifluoroacetate salt of 3-[(4-hydroxypiperidin-4-yl)methyl]-3,4-dihydroquinazolin-4-one was used in the next step without purification.

MS (ES+, mz): 260.1 [M+H]+

1H NMR (DMSO-d6) δ: 8.53 (broad m, 1H), 8.25 (s, 1H), 8.27 (broad m, 1H), 8.17 (dd, 1H), 7.85 (dd, 1H), 7.70 (dd, 1H), 7.57 (dd, 1H), 4.07 (s, 2H), 3.18 (m, 2H), 3.02 (m, 2H), 1.60 (m, 2H), 1.50 (m, 2H)

Step 4: 3-{[4-hydroxy-1-(3-phenylpropanoyl)piperidin-4-yl]methyl}-3,4-dihydroquinazolin-4-one To a solution of the TFA salt from step 3 (0.8 mmol, 1 eq) in $CH_2Cl_2$ (10 mL) was added successively DIEA (N,N diisopropylethylamine) (0.4 mL, 2.4 mmol, 3 eq), hydrocinnamic acid (150 mg, 0.96 mmol, 1.2 eq), EDCl (306 mg, 1.6 mmol, 2 eq) and HOBt (216 mg, 1.6 mmol, 2 eq). The reaction mixture was stirred at room temperature overnight and then concentrated in vacuo. The crude product was purified by flash column chromatography on silica gel (eluent: cyclohexane/ethyl acetate from 2/8 to 0/10 then ethyl acetate/MeOH 91) to give Example 1 (256 mg, 82%) as a white solid.

MS (ES+, mz): 392.2 [M+H]+

1H NMR (DMSO-d6) δ: 8.25 (s, 1H), 8.17 (dd, 1H), 7.84 (dd, 1H), 7.69 (dd, 1H), 7.55 (dd, 1H), 7.21 (m, 5H), 4.96 (s, 1H), 4.04 (m, 3H), 3.64 (m, 1H), 3.21 (m, 1H), 2.93 (m, 1H), 2.80 (m, 2H), 2.62 (m, 2H), 1.41 (m, 4H)

Example 5

3-({4-hydroxy-1-[2-methyl-3-(thiophen-2-yl)propanoyl]piperidin-4-yl}methyl)-3,4-dihydroquinazolin-4-one To a solution of the TFA salt from step 3 of example 1 (0.42 mmol, 1 eq) in $CH_2Cl_2$ (10 mL) was added successively DIEA (0.37 mL, 2.12 mmol, 5 eq), 2-Methyl-3-(2-thienyl)propanoic acid (71 mg, 0.42 mmol, 1 eq, Organometallics, 2002, 21, 2842), EDCl (161 mg, 0.84 mmol, 2 eq) and HOBt (114 mg, 0.84 mmol, 2 eq). The reaction mixture was stirred at room temperature overnight and then concentrated in vacuo. The crude product was purified by flash column chromatography on silica gel (eluent: cyclohexane/ethyl acetate from 2/8 to 0/10 then ethyl acetate/MeOH 9/1). A second purification by column chromatography was performed using the same conditions to give, after solvent evaporation and drying under high vacuum Example 5 (117 mg, 68%) as a white solid.

MS (ES+, mz): 412.2 [M+H]+

1H NMR (DMSO-d6) δ: 8.24 (s, 1H), 8.17 (m, 1H), 7.84 (m, 1H), 7.70 (m, 1H), 7.56 (m, 1H), 7.27 (m, 1H), 6.88 (m, 1H), 6.82 (s, 1H), 4.96 (s, 1H), 4.06 (m, 1H), 3.90 (m, 2H), 3.68 (m, 1H), 3.20 (m, 5H), 1.34 (m, 4H), 1.02 (m, 3H).

Example 11

7-chloro-3-({4-hydroxy-1-[2-methyl-3-(thiophen-2-yl)propanoyl]piperidin-4-yl}methyl)-3,4-dihydroquinazolin-4-one Step 1: Preparation of tert-butyl 4-[(7-chloro-4-oxo-3,4-dihydroquinazolin-3-yl)methyl]-4-hydroxypiperidine-1-carboxylate To a solution of 7-chloro-3,4-dihydroquinazolin-4-one (0.40 g, 2.2 mmol, 1 eq) in DMF (5 mL) was added compound from step 1 of example 1 (0.47 g, 1 eq) and cesium carbonate (2.17 g, 3 eq). The reaction mixture was heated at 80° C. overnight, and then allowed to reach room temperature. The mixture was washed with a saturated $NH_4Cl$ solution, and then extracted with AcOEt. The combined organic extracts were dried over $Na_2SO_4$, filtered and concentrated in vacuo. The crude product was purified by flash chromatography on silica gel (eluent: cyclohexane/ethyl acetate 3/7). A second purification by flash chromatography on silica gel was performed (eluent: cyclohexane/ethyl acetate 6/4 to 0/10) to give tert-butyl 4-[(7-chloro-4-oxo-3,4-dihydroquinazolin-3-yl)methyl]-4-hydroxypiperidine-1-carboxylate (0.6 g, 68%) as a colourless oil.

Step 2: Preparation of Trifluoroacetate salt of 7-chloro-3-[(4-hydroxypiperidin-4-yl)methyl]-3,4-dihydroquinazolin-4-one Compound from above step 1 (0.6 g, 1.5 mmol) was dissolved in TFA (5 mL) and the reaction mixture was stirred at room temperature overnight. The resulting mixture was concentrated in vacuo. The crude Trifluoroacetate salt of 7-chloro-3-[(4-hydroxypiperidin-4-yl)methyl]-3,4-dihydroquinazolin-4-one was used in the next step without purification.

Step 3: 7-chloro-3-({4-hydroxy-1-[2-methyl-3-(thiophen-2-yl)propanoyl]piperidin-4-yl}methyl)-3,4-dihydroquinazolin-4-one To a solution of the TFA salt from above step 2 (0.51 mmol, 1 eq) in CH$_2$Cl$_2$ (18 mL) was added successively DIEA (0.45 mL, 2.5 mmol, 5 eq), 2-Methyl-3-(2-thienyl) propanoic acid (86 mg, 0.51 mmol, 1 eq, Organometallics, 2002, 21, 2842), EDCl (196 mg, 1.02 mmol, 2 eq) and HOBt (138 mg, 1.02 mmol, 2 eq). The reaction mixture was stirred at room temperature overnight and then concentrated in vacuo. The crude product was purified by flash column chromatography on silica gel (eluent: cyclohexane/ethyl acetate from 2/8 to 0/10 then ethyl acetate/MeOH 9/1). A second purification by flash column chromatography on silica gel was performed to remove residual reagents. The product was solubilized in EtOH/H$_2$O 1/1 and the solution freeze-dried to give Example 11 (85 mg, 40% over two steps) as a white meringe.

MS (ES+, mz): 446.2 [M+H]+

1H NMR (DMSO-d6) δ: 8.27 (m, 1H), 8.17 (m, 1H), 7.77 (m, 1H), 7.59 (m, 1H), 7.25 (m, 1H), 6.90 (m, 1H), 6.82 (m, 1H), 4.96 (s, 1H), 4.09 (m, 3H), 3.68 (m, 1H), 3.20 (m, 5H), 1.50 (m, 4H), 1.03 (m, 3H)

Example 12

3-({4-hydroxy-1-[3-(thiophen-2-yl)propanoyl]piperidin-4-yl}methyl)-3,4-dihydroquinazolin-4-one To a solution of the TFA salt from step 3 of example 1 (0.42 mmol, 1 eq) in CH$_2$Cl$_2$ (10 mL) was added successively DIEA (0.37 mL, 2.1 mmol, 5 eq), 3-(Thiophen-2-yl) propanoic acid (80 mg, 0.51 mmol, 1.2 eq), EDCl (161 mg, 0.84 mmol, 2 eq) and HOBt (114 mg, 0.84 mmol, 2 eq). The reaction mixture was stirred at room temperature during 4 days and then concentrated in vacuo. The crude product was purified by flash column chromatography on silica gel (eluent: cyclohexane/ethyl acetate from 2/8 to 0/10 then ethyl acetate/MeOH 9/1). The product was solubilized in EtOH/H$_2$O and the solution freeze-dried to give, Example 12 (125 mg, 75%) as a white meringe.

MS (ES+, mz): 398.2 [M+H]+

1H NMR (DMSO-d6) δ: 8.24 (s, 1H), 8.16 (dd, J=8 Hz, 1H), 7.84 (dd, J=8 Hz, J=8 Hz, 1H), 7.68 (d, J=8 Hz, 1H), 7.55 (dd, J=8 Hz, J=8 Hz, 1H), 7.27 (m, 1H), 6.90 (m, 3H), 4.98 (s, 1H), 4.09 (m, 1H), 3.99 (m, 2H), 3.64 (m, 1H), 3.23 (m, 1H), 3.00 (m, 2H), 2.92 (m, 1H), 2.66 (m, 2H), 1.45 (m, 4H).

Example 13

3-{[1-(2-benzylpropanoyl)-4-hydroxypiperidin-4-yl]methyl}-3,4-dihydroquinazolin-4-one To a solution of the TFA salt from step 3 of example 1 (2.37 mmol, 1 eq) in CH$_2$Cl$_2$ (30 mL) was added successively DIEA (1.24 mL, 7.11 mmol, 7 eq), 2-methyl-3-phenylpropanoic acid (466 mg, 2.84 mmol, 1.2 eq), EDCl (909 mg, 4.74 mmol, 2 eq) and HOBt (640 mg, 4.74 mmol, 2 eq). The reaction mixture was stirred at room temperature overnight and then concentrated in vacuo. The crude product was purified by flash column chromatography on silica gel (eluent: cyclohexane/ethyl acetate from 2/8 to 0/10 then ethyl acetate/MeOH 9/1) to give Example 13 (640 mg, 66% over two steps) as a white solid.

MS (ES+, mz): 406.3 [M+H]+

1H NMR (DMSO-d6) δ: 8.20 (m, 2H), 7.84 (m, 1H), 7.68 (m, 1H), 7.56 (m, 1H), 7.20 (m, 5H), 4.90 (m, 1H), 3.85 (m, 4H), 3.11 (m, 2H), 2.82 (m, 2H), 2.52 (m, 1H), 1.48 (m, 4H), 1.00 (m, 3H).

Example 14

3-{[1-(2-benzylpropanoyl)-4-hydroxypiperidin-4-yl] methyl}-7-chloro-3,4-dihydroquinazolin-4-one To a solution of the TFA salt from step 2 of example 11 (0.34 mmol, 1 eq) in CH$_2$Cl$_2$ (10 mL) was added successively DIEA (0.18 mL, 1.02 mmol, 3 eq), 2-methyl-3-phenylpropanoic acid (67 mg, 0.41 mmol, 1.2 eq), EDCl (130 mg, 0.68 mmol, 2 eq) and HOBt (104 mg, 0.68 mmol, 2 eq). The reaction mixture was stirred at room temperature overnight and then concentrated in vacuo. The crude product was purified by flash column chromatography on silica gel (eluent: cyclohexane/ethyl acetate from 2/8 to 0/10 then ethyl acetate/MeOH 9/1) to give Example 14 (56 mg, 37% over two steps) as a white solid.

MS (ES+, mz): 440.3 [M+H]+

1H NMR (DMSO-d6) δ: 8.29 (d, J=8 Hz, 1H), 7.20 (t, J=8 Hz, 1H), 7.79 (broad s, 1H), 7.64-7.61 (m, 1H), 7.32-7.26 (m, 2H), 7.22-7.16 (m, 3H), 4.94 (d, J=6 Hz, 1H), 4.15-3.79 (m, 3H), 3.68 (t, J=14 Hz, 1H), 3.24-3.09 (m, 2H), 2.89-2.82 (m, 2H), 1.59-1.21 (m, 4H), 1.03 (d, J=6 Hz, 3H), 0.78-0.75 (m, 1H)

Representative Cysteine Proteases

USP7 Protein Production & Purification

The cDNA encoding USP7 was obtained by PCR amplification from placenta mRNA. USP7 cDNA was subcloned by PCR into a baculovirus expression vector (pFastBac-HT; Invitrogen). Full-length wild-type human USP7 and its catalytic mutant (cysteine 223 replaced by alanine, C223A) were produced as N-terminally His-tagged fusions in *Spodoptera frugiperda* cells (Sf9, Invitrogen), using the Bac-to-Bac Baculovirus system from Invitrogen according to the manufacturer's instructions. pFastBac-HT-B-USP7 was used to transform DH10bac cells (Invitrogen), and bluewhite selection was carried out on X-gal/IPTG agar plates. Bacmid DNA was prepared by an alkaline lysis procedure. The integrity of the bacmid minipreps and their orientation were checked by PCR, using generic and specific primers. Sf9 insect cells were cultured in InsectXpress medium (Cambrex) at 27° C. and transfected with the corresponding bacmid, using GeneShuttle 40 (Q-BIOgen). Viruses were recovered in the supernatant 72 h after transfection. Viruses were amplified by infecting insect cells (Sf9 or High Five cells; invitrogen) in 50 ml InsectXpress medium in a 150 cm$^2$ cell culture flask with 500 μl of the supernatant from transfected Sf9 cells. Following the second round of amplification, infected cells were recovered by rapid SDS lysis, boiled for 5 min at 100° C., sonicated briefly and centrifuged for 20 min at 14,000 g. Expression levels in infected Sf9 cells were compared with those in uninfected cells. Fusion proteins were then allowed to bind to TALON beads (BD Biosciences, TALON metal affinity resin) for 30 min at 4° C. with gentle rocking. Beads were extensively washed (50 mM sodium phosphate buffer pH 7.0, 500 mM NaCl, 10 mM Imidazole, 0.5% Triton X-100 and 10% glycerol) and bound proteins were eluted in wash buffer supplemented with 250 mM Imidazole (Sigma). Eluted fractions were resolved on 4-12% NuPAGE gels (Novex, Invitrogen). Fractions containing high concentrations of purified proteins (purity>95%) were dialyzed (20 mM Tris HCl pH 7.6, 200 mM NaCl, 1 mM DTT, 1 mM EDTA and 10% glycerol) were aliquoted and snap frozen in liquid nitrogen before storage at −80° C.

USP7 Activity Assay

USP7 was diluted in USP buffer (50 mM Tris HCl; 0.5 mM EDTA (Ethylenediaminetetraacetic acid); 5 mM DTT; 0.01% Triton X-100; Bovine Serum Albumin 0.05 mg·ml$^{-1}$ pH7.6). Compounds stocks (10 mM) were stored at −20° C. in DMSO. Compounds were tested at different concentrations: from 200 µM to 91 nM.

Reactions were performed as duplicates in Black 384 well plates (small volumes microplates; Greiner; 10 µl final reaction volume). The substrate concentration for USP7 was 300 nM Ub-AMC (*Chem. Biol.*, 2003, 10, p. 837-846) (Boston Biochem). The concentrations of the enzyme (USP7) in specificity assays was 100 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

USP5 Activity Assay

USP5 was diluted in USP buffer (50 mM Tris HCl; 0.5 mM EDTA; 5 mM DTT; 0.01% Triton X-100; Bovine Serum Albumin 0.05 mg·ml$^{-1}$ pH 7.6). Compounds stocks (100 mM) were stored at −20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for USP5 was 300 nM Ub-AMC (Boston Biochem). The concentrations of the enzyme (USP5) in specificity assays was 300 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

Cloning & Purification of USP8

The cDNA encoding USP8 was obtained by PCR amplification from placenta mRNA. USP8 cDNA was subcloned by PCR into a baculovirus expression vector (pFastBac-HT; Invitrogen). A cDNA encoding a mutated USP8 was generated by mutagenic PCR. The corresponding protein encodes a cysteine to alanine substitution at residue 786. The sequences were ascertained by sequencing of the entire open reading frame. Bacmids encoding USP8 were generated following DH10bac transposition. The corresponding bacmids were transfected into insect cells (Sf9). Viruses were recovered from culture supernatant and amplified twice. Insect cells (Sf9 or High Five; Invitrogen) were infected for 72 hours. Total cell lysates were harvested and lyzed in lysis buffer (Tris HCl 50 mM pH7.6; 0.75% NP40; 500 mM NaCl; 10% glycerol; 1 mM DTT; 10 mM imidazole; Protease Inhibitor Cocktail; AEBSF 20 µg·ml$^{-1}$; Aprotinin 10 µg·ml$^{-1}$). Proteins were affinity purified on metal affinity resins (Talon Metal affinity resin; BD Biosciences). Bound materials were extensively washed in wash buffer (50 mM Sodium Phosphate pH 7.0; 300 mM NaCl; 10 mM imidazole; 0.5% Triton X-100; 10% glycerol) and eluted from the resin in 250 mM imidazole-containing wash buffer. Proteins were dialyzed in dialysis buffer (Tris HCl pH 7.6 20 mM; NaCl 200 mM; DTT 1 mM; EDTA 1 mM; 10% Glycerol). Proteins purifications were analyzed on 4-12% NuPAGE (Invitrogen).

USP8 Activity Assay

USP8 was diluted in USP buffer (50 mM Tris HCl; 0.5 mM EDTA; 5 mM DTT; 0.01% Triton X-100; Bovine Serum Albumin 0.05 mg·ml$^{-1}$ pH8.8). Compounds stocks (100 mM) were stored at −20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for USP8 was 300 nM Ub-AMC (Boston Biochem). The concentration of the enzyme (USP8) in specificity assays was 1.36 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

UCH-L1 Activity Assay

UCH-L1 was diluted in USP buffer (50 mM Tris HCl; 0.5 mM EDTA; 5 mM DTT (Dithiothreitol); 0.01% Triton X-100; Bovine Serum Albumin 0.05 mg·ml$^{-1}$ pH7.6). Compounds stocks (100 mM) were stored at −20° C. in DMSO. Compounds were tested at different concentrations: from 200 µM to 91 nM.

Reactions were performed as duplicates in Black 384 well plates (small volume microplates; Greiner; 10 µl final reaction volume). The substrate concentration for UCH-L1 was 300 nM Ub-AMC (Boston Biochem). The concentration of the enzyme (UCH-L1) in specificity assays was 2.5 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

UCH-L3 Activity Assay

UCH-L3 was diluted in USP buffer (50 mM Tris HCl; 0.5 mM EDTA; 5 mM DTT; 0.01% Triton X-100; Bovine Serum Albumin 0.05 mg·ml$^{-1}$ pH7.6). Compounds stocks (100 mM) were stored at −20° C. in DMSO. Compounds were tested at different concentrations: from 200 μM to 91 nM.

Reactions were performed as duplicates in Black 384 well plates (small volume microplates; Greiner; 10 μl final reaction volume). The substrate concentration for UCH-L3 was 300 nM Ub-AMC (Boston Biochem). The concentration of the enzyme (UCH-L3) in specificity assays was 13 pM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/− standard deviation) were analyzed as % of control (no compound) and plotted as percentage versus the Log of the compound concentration using GraphPad (Prism). Data were fitted to a sigmoidal model (variable slope).

Caspase 3 Activity Assay

Caspase 3 was diluted in Caspase 3 buffer (100 mM Hepes pH 7.5; 10% sucrose; 0.1% CHAPS). Compounds stocks (100 mM) were stored at −20° C. in DMSO. Compounds were tested at different concentrations: from 200 μM to 91 nM.

Reactions were performed as duplicates in Black 384 well plates (small volume microplates; Greiner; 10 μl final reaction volume). The substrate concentration for caspase 3 specificity assay was 250 nM (Ac-DEVD-AMC; Promega). The concentration of the enzyme (Caspase 3) in specificity assays was 1.6 nM. The concentrations were determined in order to perform specificity assays under initial velocities at fixed substrate concentration. Compounds were pre-incubated with enzymes for 30 minutes at 25° C. Reactions were initiated by addition of substrate to the plates containing the enzymes (+/− compounds) diluted in assay buffer. Reactions were incubated for 60 minutes at 37° C. Reactions were stopped by adding acetic acid (100 mM final). Readings were performed on a Pherastar Fluorescent Reader (BMG). λ Emission 380 nm; λ Excitation=460 nm. Data (mean values+/−standard deviation) were analyzed as % of control (no compound) and plotted as percentage versus the Log of the compound concentration using GraphPad (Prism). Data were fitted to a sigmoidal model (variable slope).

Cell Viability and Proliferation Methods

HCT116 Cell Viability and Proliferation Assay

HCT116 colon cancer cells were obtained from ATCC (American Type Culture Collection), and maintained in Mc Coy's 5A medium containing 10% FBS, 3 mM glutamine and 1% penicillin/streptomycin. Cells were incubated at 37° C. in a humidified atmosphere containing 5% $CO_2$.

Cell viability was assayed using the MTS technique in 96-well culture plates (CellTiter 96® Aqueous Non-Radioactive Cell Proliferation Assay, Promega) according to the manufacturer's instructions. MTS (3-(4,5-dimethyl-thiazol-2-yl)-5-(3-carboxy-methoxyphenyl)-2-(4-sulfophenyl)-2H-tetra-zolium) is a MTT-derived tetrazolium that is reduced in metabolically active cells into a soluble, cell-permeant formazan. The amount of formazan, detected by its absorbance at 492 nm is proportional to the number of living, metabolically active cells.

$10^3$ HCT116 cells were seeded per well. 24 hours later, the medium was changed and the cells treated in triplicate with the concentrations of each compound from 100 μM to 50 nM. The compounds were diluted in 100% DMSO, whose final concentration on cells was kept at 0.5%.

Cells were incubated with the compounds for 72 hours, and their viability then assayed by the addition of MTS for 2 hours. Absorbance at 492 nm was measured directly from the 96-well culture plates. GI50 (Growth Inhibition 50) concentrations for each compound were calculated using a sigmoidal variable slope fit (Prism 4.0, Graphpad Softwares). Values represent mean of three independent experiments.

Methods for Evaluation of Compound Selectivity from a Panel of Deubiquitinating Enzymes Active in Cell Lysates The C-terminally modified vinyl sulfone derivative of ubiquitin, UbVS, was clearly helpful for a direct visualization of active DUBs in cells. This tool, which binds covalently to the cysteine active site of deubiquitinating enzymes, was successfully applied to discover and characterize novel ubiquitin/ubiquitin-like proteases and to profile active deubiquitinating enzymes in normal, virus-infected, and malignant cells (Borodovsky et al., *Chem Biol* 2002, 9, 1149-1159, Hemelaar et al., *Mol Cell Biol* 2004, 24, 84-95, Ovaa et al., *Proc Natl Acad Sci USA* 2004 101, 2253-2258).

The HA-Ub-VS probe (Hemagglutin tag-Ubiquitin-Vinyl Sulfone) was used in this study to directly visualize the activity of all deubiquitinating enzymes from native proteomes. This tool was used to evaluate the activity/specificity of our small molecule compounds on USP7 relative to all deubiquitinating enzymes active in physiological conditions.

HEK293 cells were harvested and lysed on ice with a non denaturating buffer containing Tris pH7.4, 50 mM; NaCl, 150 mM; $MgCl_2$, 5 mM; EDTA, 0.5 mM; DTT, 2 mM; ATP (adenosine triphosphate), 2 mM; NP40 (nonyl phenoxypoly-ethoxylethanol), 0.5% and glycerol, 10%. Samples were incubated at 4° C. for 1 hour and clarified. Proteins were then quantified by Bradford method (Bio-Rad Protein Assay). 50 μg of proteins from native cell lysates were treated with compounds of examples 1 and 2 (from 12.5 μM to 200 μM) or with a non-specific DUB inhibitor as control for 2 hours at room temperature. The ubiquitin labeling reaction was initiated by the addition of HA-Ub-VS (8 μg/ml) in labeling buffer (Tris pH7.6, 50 mM; $MgCl_2$, 5 mM; EDTA, 0.5 mM; DTT, 2 mM; ATP, 2 mM; sucrose, 250 mM) and incubated at room temperature for 15 min. Samples were next heated at 100° C. for 10 minutes and briefly sonicated. They were resolved by SDS-polyacrylamide gel electrophoresis (SDS-PAGE), transferred to a nitrocellulose membrane and probed with antibodies against USP7, HA, UCH-L3, CYLD, USP8, USP5, USP10 and Stat3. Horseradish peroxidase (HRP)-conjugated anti-mouse (Jackson Laboratories, 115-035-003) or HRP-conjugated anti-rabbit (Cell Signaling, 7074) antibodies were used as secondary antibodies. Signals were detected by enhanced chemiluminescence (ECL; Amersham) according to the reagent manufacturer's instructions.

Results

1. Use of Ub52 as USP7 and USP8 Substrate for Evaluation of USP Modulators

For the composition according to the invention, the in vitro assays on USP7 and USP8 were carried out according to the following procedure Preparation of Ubiquitin-Ribosomal Protein Fusions A cDNA encoding the fusion protein between ubiquitin and the ribosomal protein L40 (ub52 or uba52 or ubiquitin-L40) was amplified from human RNA using a proprietary human placenta library. The cDNA was subcloned into a bacterial expression vector (pGEX-2T, GE Healthcare), including an additional flag tag at the carboxyl end of the encoded protein. The following primers were used for subcloning in frame with the GST tag the ubiquitin-L40 into pGEX-2T: 5'-cgtggatccatgcagatctttgtgaagaccctc-3' (SEQ ID NO:1) and 5'-gcgaattctttatcgtcatcgtctttgtagtctttgaccttcttct-tgggacg-3' (SEQ ID NO:2) into BamHI & EcoRI restriction sites.

For production and purification of recombinant proteins, the plasmid pGEX-2T-Ub52-flag was transformed into E. coli BL21 (Stratagene), grown in LB medium supplemented with 100 mg/ml ampicillin (LB ampi) at 37° C. overnight and then diluted 1/100 in LB ampi. The cells were incubated at 37° C. until an A600=0.6-0.8 was reached. After induction with 0.1 mM isopropyl-β-D-thiogalactopyranoside (IPTG), the culture was incubated at 30° C. for 180 min.

Cells were harvested by centrifugation for 15 min at 7000×g at 4° C. Bacterial pellets were lysed in NETN (Tris HCl pH 8.0; EDTA 1 mM; NP40 0.5%; protease inhibitor cocktail, PMSF 1 mM) and briefly sonicated. Insoluble material was removed by centrifugation 30 min at 14000×g. GST-Ub52-flag proteins were purified according to Everett R D et al., EMBO J. (1997) 16, 1519-1530. Briefly, soluble fraction was incubated on Glutathione beads pre-equilibrated in NETN buffer+0.5% Milk for 120 min at 4° C. Flow Through was recovered. Beads were extensively washed: the last wash performed in Tris HCl pH 7.6 20 mM; NaCl 100 mM; MgCl$_2$ 12 mM. Elutions were performed using 20 mM Reduced Glutathione in 50 mM Tris HCl pH 8.0, NaCl 120 mM. All fractions were resolved on a 4-12% NuPAGE following 0.1 M DTT treatment and denaturation and stained with Coomassie Brilliant Blue. Elutions were dialysed over night at 4° C. in Tris HCl pH 7.6 20 mM; NaCl 50 mM; DTT 0.5 mM.

Assaying the Fusion Protein (GST-Ub52-Flag) Using Homogenous Time-Resolved Fluorescence (HTRF®) Measurement Method The use of GST-Ub52-Flag is based on the time-resolved measurement of fluorescence emitted by transfer in homogenous medium.

The reagents used were as follows:
Anti-flag antibody-europium cryptate conjugate referred to as anti-Flag-K (CIS bio international), solution at 0.2 µM in 0.8 M KF, 0.1% Bovine Serum Albumin, Tris HCl 25 mM pH 7.6.
Anti-GST antibody-XL665 conjugate (CIS bio international), solution at 2.6 µM in 0.8 M KF, 0.1% Bovine Serum Albumin, Tris HCl 25 mM pH 7.6.
GST-Ub52-Flag solution at 14.75 µM & MBP_Ub52 at 37.7 µM prepared from the stock solution described above in 50 mM Tris HCl pH 7.6, EDTA 0.5 mM, Bovine Serum Albumin 0.05%, DTT 5 mM.

The assay is carried out on multiwell assay plates. The plates are analyzed on a PHERAstar fluorimeter (BMG) after an overnight incubation at 4° C. (excitation 337 nm, emission 620 and 665 nm).

Assaying the Activity of Enzymes of the Deubiquitinating Type with Ubiquitin-Ribosomal Protein Fusion The reagents used were as follows:
Solution of USP7 at 200 pM and USP8 at 400 pM in 50 mM Tris HCl pH 7.6, Bovine Serum Albumin 0.05%, DTT 5 mM.
Anti-Flag-K (CIS bio international), solution at 0.2 µM in 0.8 M KF, 0.1% Bovine Serum Albumin, Tris HCl 25 mM pH 7.6.
Anti-GST antibody-XL665 conjugate (CIS bio international), solution at 2.6 µM in 0.8 M KF, 0.1% Bovine Serum Albumin, Tris HCl 25 mM pH 7.6.
GST-Ub52-flag solution at 14.75 µM & MBP_Ub52 at 37.7 µM are prepared by dilutions from the stock solution described above in 50 mM Tris HCl pH 7.6, EDTA 0.5 mM, Bovine Serum Albumin 0.05%, DTT 5 mM.

The enzyme reaction is carried out by mixing GST-Ub52-flag solution with 5 µl of USP7 solution (200 pM final) or 5 µl of USP8 (400 pM final). This mixture is incubated for one hour at room temperature on a multiwell assay plate. A 10 µl mixture of 5 µl of anti-Flag-K solution (0.2 µM) plus 5 µl of anti-GST-XL665 antibody (2.6 µM) is added to each well of the multiwell assay plate. The plate is read after an overnight incubation at 4° C. on a PHERAstar fluorimeter (BMG).

The decrease in the signal correlates with the increase in enzyme activity i.e. the cleavage of GST-Ub52-Flag substrate. The format used is therefore entirely suitable for a method of assaying an enzyme of the deubiquitinating type such as ubiquitin specific protease, but also for determining a modulator of this enzyme activity.

Determination of a Modulator of Enzyme Activity of the Deubiquitinating Type

The same procedures as mentioned above for assaying the activity of enzymes of the deubiquitinating type are carried out but the various reaction mixtures are incubated with identical enzyme concentration, in the presence or absence of compounds 1 to 14. Data (mean values+/−standard deviation) were analyzed as % of control (no compound) and plotted as percentage versus the Log of the compound concentration using GraphPad (Prism). Data were fitted to a sigmoidal model (variable slope) and IC$_{50}$ (µM) was determined and presented in the following table.

| Example | LCMS: m/z [M + H]+ | USP7 | USP8 |
|---|---|---|---|
| 1 | 392.09 | 74 | >200 |
| 2 | 426.08 | 77 | >200 |
| 3 | 384.14 | 175 | >200 |
| 4 | 418.12 | 173 | >200 |
| 5 | 412.20 | 36 | >200 |
| 6 | 330.00 | >200 | >200 |
| 7 | 390.10 | 174 | >200 |
| 8 | 412.09 | 224 | >200 |
| 9 | 391.98 | 214 | >200 |
| 10 | 422.15 | >200 | >200 |
| 11 | 446.20 | 33 | >200 |
| 12 | 398.20 | 42 | >200 |
| 13 | 406.30 | 12 | >200 |
| 14 | 440.30 | 29 | >200 |

2. Selective Inhibition of USP7 Deubiquitinating Activity Using UbAMC Substrate

The results are summarized on the following table (µM):

| Example | USP7 | USP8 | USP5 | Uch-L1 | Uch-L3 | Caspase 3 |
|---|---|---|---|---|---|---|
| 1 | 69 | >200 | >200 | >200 | >200 | >200 |
| 2 | 33 | >200 | >200 | >200 | >200 | >200 |
| 3 | 100 | >200 | >200 | >200 | >200 | >200 |
| 4 | 54 | >200 | >200 | >200 | >200 | >200 |
| 5 | 37 | >200 | >200 | >200 | >200 | >200 |
| 6 | 156 | >200 | >200 | >200 | >200 | >200 |
| 7 | 90 | >200 | >200 | >200 | >200 | >200 |
| 8 | nd | nd | nd | nd | nd | nd |
| 9 | 155 | >200 | >200 | >200 | >200 | >200 |
| 10 | 261 | >200 | >200 | >200 | >200 | >200 |
| 11 | 40 | >200 | >200 | >200 | >200 | >200 |
| 12 | 70 | >200 | >200 | >200 | >200 | >200 |

-continued

| Example | USP7 | USP8 | USP5 | Uch-L1 | Uch-L3 | Caspase 3 |
|---|---|---|---|---|---|---|
| 13 | 15 | >200 | >200 | >200 | >200 | >200 |
| 14 | 24 | >200 | >200 | >200 | >200 | >200 | nd: not determined due to autofluorescence at 460 nm

3. Inhibition of Cell Viability/Proliferation

The results are summarized on the following table (μM):

| Example | Cell viability (MTS): HCT116 GI50 Day 3 |
|---|---|
| 1 | >500 |
| 2 | 67 |
| 3 | 93 |
| 4 | 19 |
| 5 | 113 |
| 6 | nd |
| 7 | >500 |
| 8 | nd |
| 9 | nd |
| 10 | nd |
| 11 | 25 |
| 12 | 253 |
| 13 | 103 |
| 14 | 28 |

Figure 2:
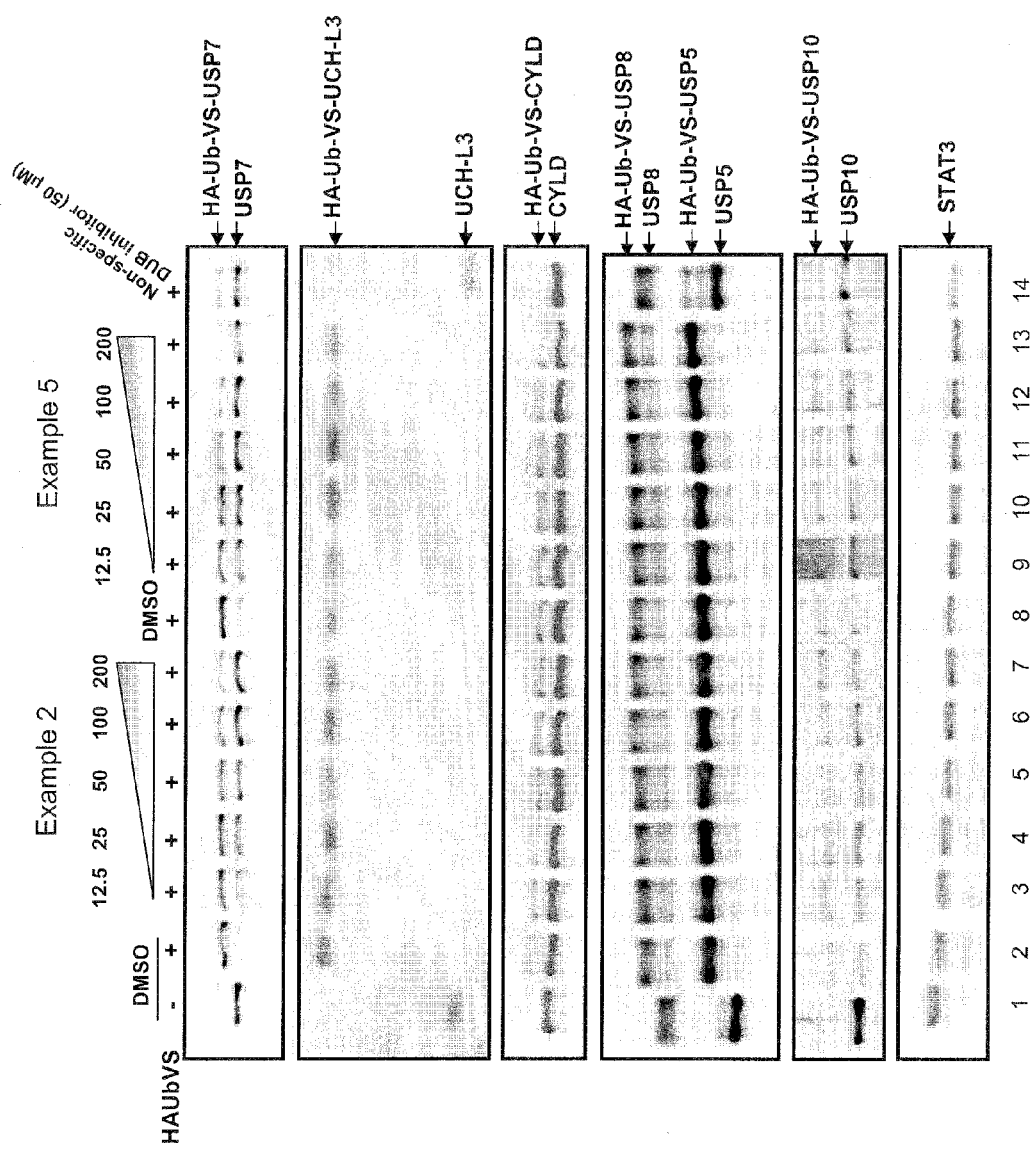
FIG. 2 shows competitive HAUbVS gels comparing the activity of example 2 and example 5 against USP7 and additional deubiquitinating enzymes (USP5, USP8, USP10, CYLD, UCH-L3) using the HEK293 proteome.

4. Selective Inhibition of USP7 Deubiquitinating Activity Over a Panel of Active DUBs in Physiological Conditions:

To confirm the specificity observed in vitro from recombinant enzymes, we performed competition assays using the HAUbVS activity-based probe (ABP) which binds covalently to the cysteine active site of deubiquitinating enzymes (Borodovsky et al., *Chem Biol* 2002, 9, 1149-1159, Hemelaar et al., *Mol Cell Biol* 2004, 24, 84-95, Ovaa et al., *Proc Natl Acad Sci USA* 2004 101, 2253-2258). In comparison with recombinant enzymes, this assay has the advantage to evaluate the effect of inhibitor against numerous deubiquitinating enzymes in parallel directly in native proteomes through Western blot analysis by using an anti-HA antibody. In this assay, the inhibitor is added to total cell lysate and inhibition is determined by the labeling of residual active deubiquitinating enzymes with the HAUbVS. This labeling followed by immunoblot with the anti-HA antibody allowed the identification of all active deubiquitinating enzymes from HEK293 cell lysates (FIG. 1, lane 2). This labeling, specific to the active form of DUBs, is inhibited by a non-specific DUB inhibitor in a non-selective manner (FIG. 1, lane 14). When lysed HEK293 cells were treated with HAUbVS in the absence and presence of different doses of examples 2 and 5, no change was noted in the immunoblot pattern with the exception of one band which was almost completely eliminated at the size corresponding to HA-Ub-VS-USP7 (FIG. 1). This effect on USP7 activity was confirmed with anti-USP7 antibody as indicated by the mobility shift observed between the treated and non-treated samples (FIG. 2).

We next evaluated the effect of USP7 inhibitors on the HAUbVS labelling efficiency by monitoring individually several deubiquitinating enzymes. To this end, HAUbVS labeling efficiency on USP7, USP8, USP5, USP10, CYLD and UCH-L3 from HEK293 cell lysates was first checked using specific antibodies. This labeling was confirmed with all tested DUBs, as indicated by the mobility shift observed between the HAUbVS-treated and non-treated samples, albeit with different efficiency rates (FIG. 2, lanes 1 and 2). Potential inhibition of these DUBs was evaluated in the presence of examples 2 and 5 as well as non-specific DUB inhibitor as control. As expected, we found that the non-specific DUB inhibitor inhibited all tested DUBs (FIG. 2, lane 14). Interestingly, we found that examples 2 and 5 efficiently blocked labeling of USP7 but not USP8, USP5, USP10, CYLD or UCH-L3, showing its USP7 specificity over a panel of active DUBs in physiological conditions (FIG. 2). These data taken together indicate that examples 2 and 5 target directly USP7 in native proteomes in physiological conditions and in a dose-dependent manner without any cross-reaction with all tested deubiquitinating enzymes.

5. USP7-Specific Compounds are Reversible Inhibitors

Figure 3:
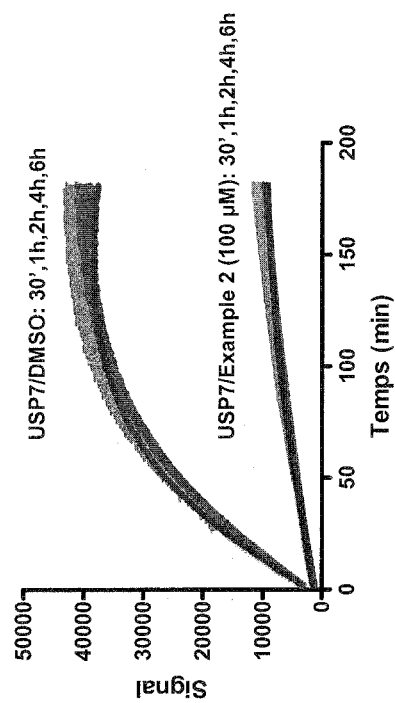
FIG. 3 shows time-dependent experiments with USP7 and example 2.

To better understand the mechanism of inhibition of USP7 by our USP7-specific compounds, several experiments were performed. We first characterized the inhibitory mechanism of example 2 by pre-incubating example 2 (100 μM) with USP7 (100 pM) at different time points (30 min, 1 h, 2 h, 4 h, 6 h). The deubiquitinating activity was then assessed with the Ub-AMC substrate, as described above, and compared with that of samples treated with DMSO. Interestingly, USP7 inhibition by example 2 (~75%) was found to be independent of the pre-incubation timing (FIG. 3). These data clearly show that example 2 is not a time-dependent inhibitor of USP7.

Figure 4:
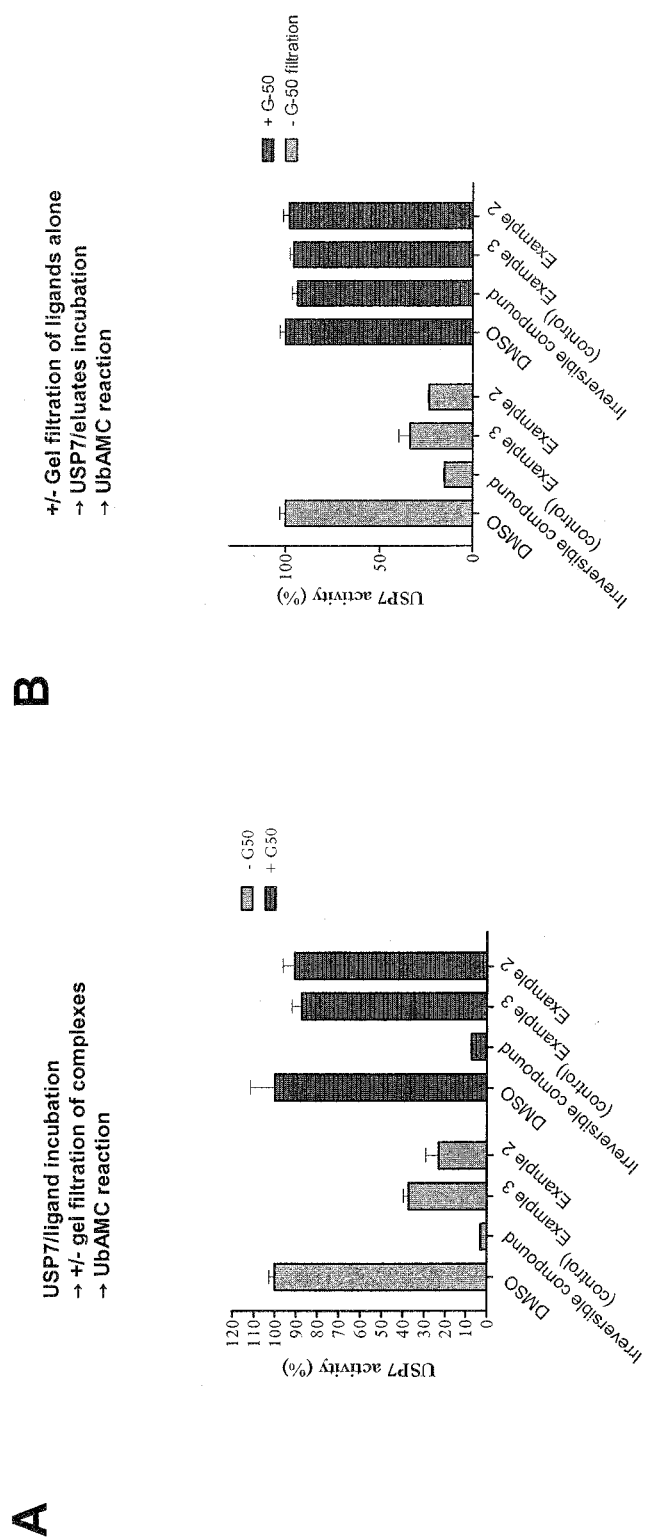
FIG. 4 shows reversibility results obtained following gel filtration experiments with USP7 in the presence of example 2 and example 3.

The reversibility of inhibition was next determined by measuring the recovery of enzymatic activity after gel filtration. We incubated USP7 (100 pM) for 4 h at room temperature in the presence of examples 2 and 3 (100 μM) or a control compound used as irreversible USP7 inhibitor (25 μM). We passed some of each sample through a G50 gel filtration system (Sephadex, G50 superfine, Sigma Aldrich). The deubiquitinating activity of the G50 eluates was assessed with the Ub-AMC substrate, as described above, and compared with that of samples not subjected to G50 filtration. The reactions were monitored using the PHERAstar (BMG Labtech). In the absence of filtration, USP7 activity was inhibited by examples 2 and 3 and by a control inhibitor used as irreversible compound (FIG. 4A, −G50). Using samples containing these compounds alone, we confirmed that all compounds, filtered through a G50 column, were entirely retained on the column (FIG. 4B). The filtration of samples containing USP7 and examples 2 and 3 through a G50 column led to the total restoration of USP7 activity, whereas USP7 inhibition by the irreversible control compound could not be reversed by filtration (FIG. 4A, +G50). Since an irreversible complex is expected to remain inhibited after washing, our findings demonstrate that examples 2 and 3 are reversible USP7 inhibitors.

Figure 5:
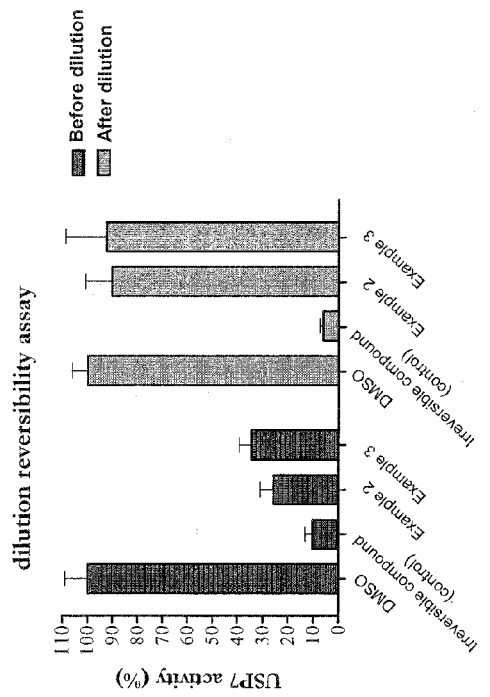
FIG. 5 shows reversibility results obtained following rapid and large dilution of USP7 in the presence of example 2 and example 3.

To confirm these findings, we measured the recovery of enzymatic activity after a rapid and large dilution of the enzyme-compound complex. We incubated USP7 at a concentration of 100-fold (10 nM) over the concentration required for the activity assay, with a concentration of inhibitor equivalent to 10-fold the $IC_{50}$ (FIG. 5A). After a reasonable equilibration timing (1 h), this mixture is diluted 100-fold into reaction buffer containing UbAMC (300 nM) to initiate the reaction (FIG. 5A). Dilution of samples containing USP7 and examples 2 and 3 led to the almost total restoration of USP7 activity, whereas USP7 inhibition by the irreversible control compound could not be reversed by dilution (FIG. 5B). The dissociation of examples 2 and 3 from USP7 leading to restoration of greater than approximately 90% of enzymatic activity following rapid and large dilution clearly demonstrates that examples 2 and 3 are rapid reversible inhibitors.

Figure 6:
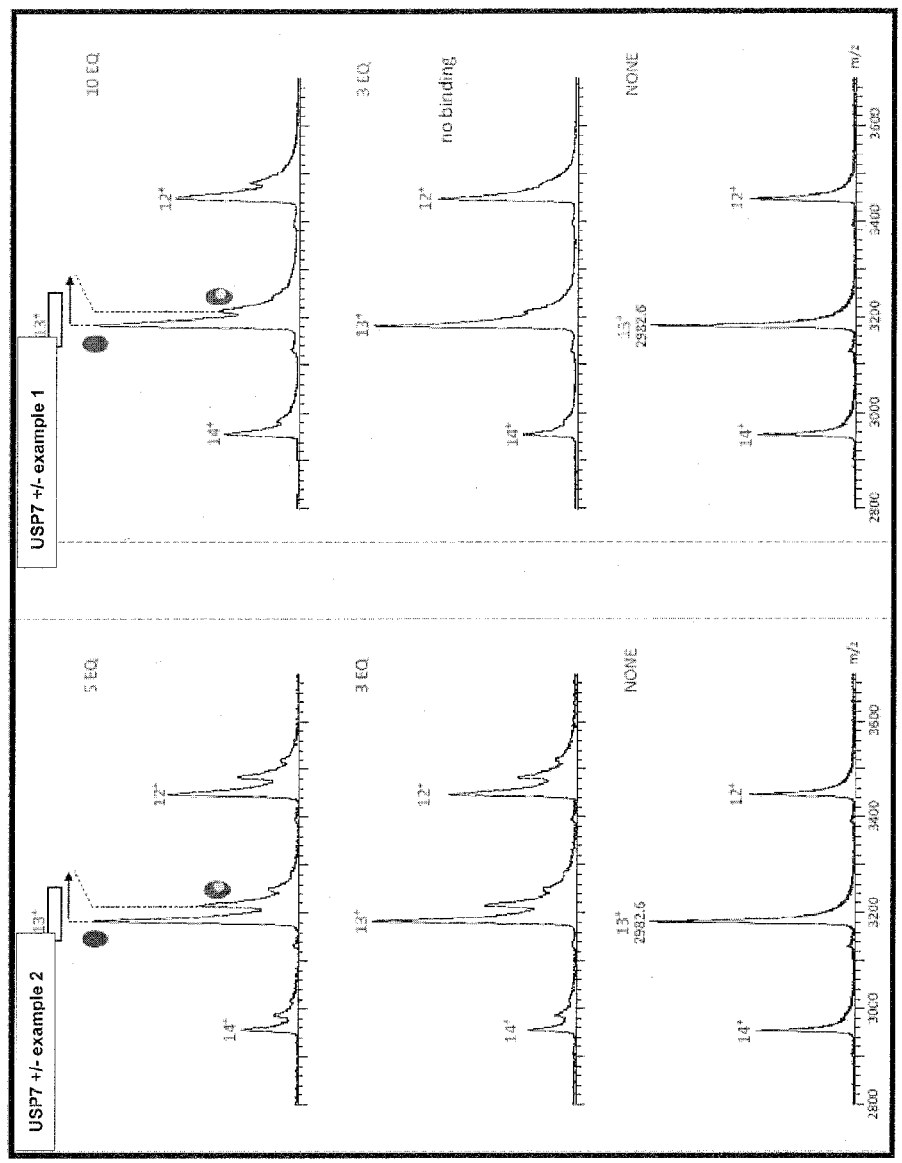
FIG. 6 represents characterization of complexes involving USP7 and examples 1 and 2 as evaluated by ESI-MS in native conditions.

To characterize complexes involving USP7 and examples 1, 2, 3 and 5, we evaluated the direct binding by ESI-MS in native conditions (7 mM ammonium acetate pH 7.5), as previously described (Vivat Hannah et al., *Future Med Chem.* 2010 2(1):35-50). We first checked the interaction by incubating the protein in the presence of 3-5-10 molar equivalents of examples 1, 2, 3 and 5. All these compounds formed complexes with USP7 to various extends and showed 1:1 binding stoichiometry to USP7 when tested at 3 or 5 molar equivalent excess, as illustrated with examples 1 and 2 in FIG. 6. No difference of mass of compounds was observed in the presence or absence of USP7. In order to dissociate weak non-covalent complexes, USP7/inhibitor complexes were diluted in 50/50/1 H2O/CH3CN/HCOOH and analyzed under energetic instrumental conditions (Vc=120 V, Pi=4 mbar). In these conditions, no binding was observed between USP7 and examples 1, 2, 3 and 5 suggesting that USP7 and examples 1, 2, 3 and 5 form non-covalent complexes.

All these data clearly indicate that these USP7-specific inhibitors bind USP7 through a reversible manner.

The invention claimed is:

1. A compound of formula (I'):

wherein $R^1$, each identical or different, is selected from the group consisting of halogen, linear or branched ($C_1$-$C_6$) alkyl, OR, NRR', CN, CF$_3$, C(O)R, C(O)OR, C(O)NRR', NO$_2$, ($C_1$-$C_6$)alkylene-OR, ($C_1$-$C_6$) alkylene-NRR', ($C_1$-$C_6$)alkylene-CO$_2$R, ($C_1$-$C_6$) alkylene-CONRR', —O—($C_1$-$C_6$)alkylene-CO$_2$R, —O—($C_1$-$C_6$)alkylene-CONRR', CO$_2$—($C_1$-$C_6$) alkylene-OR, CO$_2$—($C_1$-$C_6$)alkylene-NRR', C(O)NH—($C_1$-$C_6$)alkylene-OR, CONH—($C_1$-$C_6$)alkylene-NRR', and NHC(O)R;

$L^1$ is linear or branched ($C_1$-$C_6$)alkylene optionally substituted by one or more of =O, CN, C(O)R, C(O)OR, or C(O)NRR', or linear or branched CH$_2$ ($C_1$-$C_6$)alkylene, wherein the later ($C_1$-$C_6$)alkylene is optionally substituted by one or more of halogen, OR, NRR' or CF$_3$;

q is 0, 1, 2, 3 or 4;

X' is CR$^7$;

$R^7$ is OR, halogen, linear or branched ($C_1$-$C_6$)alkyl-OR, C(O)OR, C(O)NRR', CN or OPO$_3$H$_2$;

n is 0, 1 or 2;

p is 1, 2 or 3;

$R^3$, $R^4$, $R^{8'}$ and $R^8$, each identical or different, are selected from the group consisting of H, linear or branched ($C_1$-$C_6$)alkyl, halogen, OH, —O—($C_1$-$C_6$) alkyl, NRR', CN, CF$_3$, OR, C(O)R, C(O)OR and C(O)NRR';

A is selected from the group consisting of —C(O)—, —C(O)NH—, —S(O)$_2$— and —S(O)$_2$NH—;

$L^2$ is linear or branched ($C_1$-$C_6$)alkylene optionally interrupted by at least one heteroatom selected from the group consisting of O, N and S and/or optionally substituted by: R, OR, NRR', ($C_1$-$C_6$)alkyl-OR, ($C_1$-$C_6$)alkyl-NRR', OC(O)R, NHC(O)R, NHC(O)NRR', CN or C(=NH)NHOR;

$R^6$ is selected from the group consisting of H, aryl, heteroaryl, cycloalkyl and heterocyclyl, wherein the aryl, heteroaryl, cycloalkyl or heterocyclyl is monocyclic or polycyclic and is optionally substituted by one or more of linear or branched ($C_1$-$C_6$)alkyl, halogen, NRR', CN, CF$_3$, OR, =O, C(O)R, C(O) OR, NHC(O)R, OC(O)R or C(O)NRR'; and each R and R', identical or different, are independently selected from the group consisting of H, linear or branched ($C_1$-$C_6$)alkyl, aryl, heterocyclyl, heteroaryl, linear or branched —($C_1$-$C_6$)alkyl-aryl, linear or branched —($C_1$-$C_6$)alkyl-heterocyclyl and linear or branched —($C_1$-$C_6$)alkyl-heteroaryl;

or a pharmaceutically acceptable salt, stereoisomer or tautomer thereof;

with the exception of:
(i) q is 0, L' is CH$_2$, X' is CR$^7$, where R$^7$ is OH, A is —C(O)—, L$^2$ is CH$_2$CH$_2$ and R$^6$ is 3-methylpiperidin-1-yl; and
(ii) q is 1, L' is CH$_2$, X' is CR$^7$, where R$^7$ is OH, A is —C(O)—, L$^2$ is CH(CH$_2$CH$_3$)$_2$ and, at C-7, R$^1$— is Cl.

2. The compound according to claim 1, wherein A is —C(O)—.

3. The compound according to claim 1, wherein L$^1$ is CH$_2$.

4. The compound according to claim 1, wherein L$^2$ is linear or branched ($C_1$-$C_6$)alkylene.

5. The compound according to claim 1, wherein $R^1$, each identical or different, is selected from the group consisting of linear or branched ($C_1$-$C_6$)alkyl, halogen, OR, NRR', CN, $CF_3$, C(O)R, C(O)OR, C(O)NRR' and NHC(O)R.

6. The compound according to claim 1, wherein $R^1$, each identical or different, is selected from the group consisting of linear or branched $C_1$-$C_6$(alkyl), halogen, OH and linear or branched —O—($C_1$-$C_6$)alkyl.

7. The compound according to claim 1, wherein $R^3$, $R^4$, $R^8$, and $R^{8'}$, each identical or different, are selected from the group consisting of H, —O—($C_1$-$C_6$)alkyl, and OH.

8. The compound according to claim 1, wherein $R^6$ is selected from the group consisting of aryl, heteroaryl, cycloalkyl and H, wherein the aryl, heteroaryl or cycloalkyl is optionally substituted by halogen or linear or branched O—($C_1$-$C_6$)alkyl.

9. The compound according to claim 1, wherein $R^7$ is OR or $OPO_3H_2$.

10. The compound according to claim 1, wherein $R^7$ is OH.

11. The compound according to claim 1, wherein p is 2 and n is 2.

12. The compound according to claim 1, wherein the sum of p and n is 4.

13. The compound according to claim 1, selected from the group consisting of:
 3-({4-hydroxy-1-[3-(2-methoxyphenyl)propanoyl]piperidin-4-yl}methyl)-3,4-dihydroquinazolin-4-one;
 3-({1-[2-(3-fluorophenoxy)acetyl]-4-hydroxypiperidin-4-yl}methyl)-3,4-dihydroquinazolin-4-one;
 3-{[4-hydroxy-1-(2-methylpropanoyl)piperidin-4-yl]methyl}-6, 7-dimethoxy-3,4-dihydroquinazolin-4-one;
 3-{[4-hydroxy-1-(2-methylpropanoyl)piperidin-4-yl]methyl}-3,4-dihydroquinazolin-4-one;
 4-hydroxy-1-([2-methyl-3-(thiophen-2-yl)propanoyl]piperidin-4-yl}methyl)-3,4-dihydroquinazolin-4-one;
 7-chloro-3-{[1-(3-cyclopentylpropanoyl)-4-hydroxypiperidin-4-yl]methyl}-3,4-dihydroquinazolin-4-one;
 3-{[1-(3-cyclopentylpropanoyl)-4-hydroxypiperidin-4-yl]methyl}-3,4-dihydroquinazolin-4-one;
 7-chloro-3-{[4-hydroxy-1-(3-phenylpropanoyl)piperidin-4-yl]methyl}-3,4-dihydroquinazolin-4-one;
 3-{[4-hydroxy-1-(3-phenylpropanoyl)piperidin-4-yl]methyl}-3,4-dihydroquinazolin-4-one;
 7-chloro-3-({4-hydroxy-1-[2-methyl-3-(thiophen-2-yl)propanoyl]piperidin-4-yl}methyl)-3,4-dihydroquinazolin-4-one;
 3-({4-hydroxy-1-[3-(thiophen-2-yl)propanoyl]piperidin-4-yl}methyl)-3,4-dihydroquinazolin-4-one;
 3-{[1-(2-benzylpropanoyl)-4-hydroxypiperidin-4-yl]methyl}-3,4-dihydroquinazolin-4-one; and
 3-{[1-(2-benzylpropanoyl)-4-hydroxypiperidin-4-yl]methyl}-7-chloro-3,4-dihydroquinazolin-4-one;
or a pharmaceutically acceptable salt, stereoisomer, or tautomer thereof.

14. A process for preparing a compound of formula (I') according to claim 1,

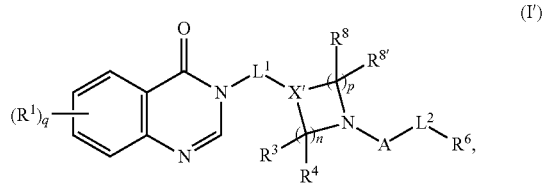

comprising the step of:
reacting a compound of formula (IIa)

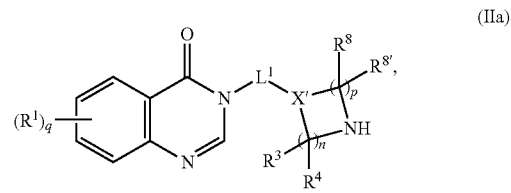

wherein n, p, q, $L^1$, $R^1$, $R^3$, $R^4$, $R^8$, $R^{8'}$ and X' are as defined in claim 1,
with a compound of formula (III)

$$Y-A-L^2-R^6 \quad (III),$$

wherein Y is halogen, OH, tosylate or mesylate and A, $L^2$ and $R^6$ are as defined in claim 1.

15. A process for preparing a compound of formula (I') according to claim 1,

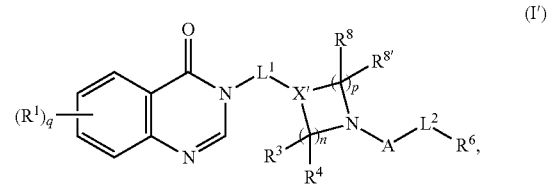

comprising the step of:
reacting a compound of formula (IV)

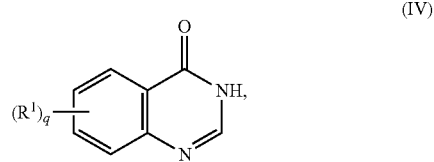

wherein q and $R^1$ are as defined in claim 1,
with a compound of formula (Va)

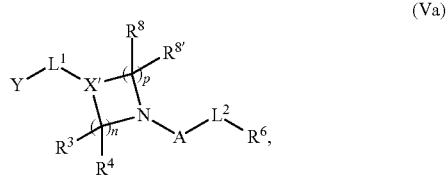

wherein Y is epoxy, halogen, tosylate or mesylate and n, p, A, $L^1$, $L^2$, $R^3$, $R^4$, $R^6$, $R^8$, $R^{8'}$ and X' are as defined in claim 1.

16. A compound of formula (I')

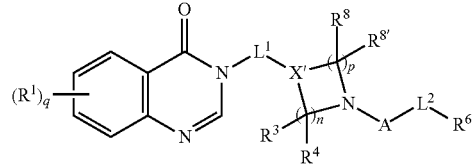

wherein
- each identical or different, is selected from the group consisting of halogen, R, OR, NRR', CN, $CF_3$, C(O)R, C(O)OR, C(O)NRR', $NO_2$, $(C_1$-$C_6)$alkylene-OR, $(C_1$-$C_6)$alkylene-NRR', $(C_1$-$C_6)$alkylene-$CO_2$R, $(C_1$-$C_6)$alkylene-CONRR', —O—$(C_1$-$C_6)$alkylene-$CO_2$R, —O—$(C_1$-$C_6)$alkylene-CONRR', $CO_2$—$(C_1$-$C_6)$alkylene-OR, $CO_2$-$(C_1$-$C_6)$alkylene-NRR', C(O)NH—$(C_1$-$C_6)$alkylene-OR, CONH—$(C_1$-$C_6)$alkylene-NRR', $OCF_3$, $SO_2$R, $SO_3$H, $SO_2$NR, $NHSO_2$R, C≡CH, $(R^{10})$C═C$(R^{11})_2$, $(R^{10})_2$C═C$(R^{11})$, $(C_1$-$C_6)$alkylene-COR, NHC(O)R, and $(C_1$-$C_6)$alkyl interrupted by at least one heteroatom selected from the group consisting of O, N and S;
- $L^1$ is linear or branched $(C_1$-$C_6)$alkylene optionally substituted by one or more of ═O, CN, C(O)R, C(O)OR, or C(O)NRR', or linear or branched $CH_2$ $(C_1$-$C_6)$alkylene, wherein the later $(C_1$-$C_6)$alkylene is optionally substituted by one or more of halogen, OR, NRR' or $CF_3$;
- q is 0, 1, 2, 3 or 4;
- X' is $CR^7$;
- $R^7$ is OR, halogen, linear or branched $(C_1$-$C_6)$alkyl-OR, C(O)OR, C(O)NRR', CN, $OR^9$, NRR' or SR;
- n is 0, 1 or 2;
- p is 1, 2 or 3;
- $R^3$, $R^4$, $R^{8'}$ and $R^8$, each identical or different, are selected from the group consisting of H, linear or branched $(C_1$-$C_6)$alkyl, halogen, OH, —O—$(C_1$-$C_6)$alkyl, NRR', CN, $CF_3$, OR, C(O)R, C(O)OR and C(O)NRR';
- A is selected from the group consisting of —C(O)—, —C(O)NH—, —S(O)$_2$— and —S(O)$_2$NH—;
- $L^2$ is linear or branched $(C_1$-$C_6)$alkylene optionally interrupted by at least one heteroatom selected from the group consisting of O, NR and S and/or optionally substituted by: R, OR, NRR', $(C_1$-$C_6)$alkyl-OR, $(C_1$-$C_6)$alkyl-NRR', OC(O)R, NHC(O)R, NHC(O)NRR', CN or C(═NH)NHOR;
- $R^6$ is selected from the group consisting of aryl, heteroaryl, cycloalkyl, heterocyclyl and H, wherein the aryl, heteroaryl, cycloalkyl or heterocyclyl is monocyclic or polycyclic and is optionally substituted by one or more of linear or branched $(C_1$-$C_6)$alkyl, halogen, NRR', CN, $CF_3$, OR, ═O, C(O)R, C(O)OR, NHC(O)R, OC(O)R, linear or branched $(C_2$-$C_6)$alkenylene or C(O)NRR';
- each R and R', identical or different, are independently selected from the group consisting of H, linear or branched $(C_1$-$C_6)$alkyl, cycloalkyl, aryl, heterocyclyl, heteroaryl, linear or branched —$(C_1$-$C_6)$alkyl-aryl, linear or branched —$(C_1$-$C_6)$alkyl-heterocyclyl and linear or branched —$(C_1$-$C_6)$alkyl-heteroaryl, wherein the heterocyclyl or heteroaryl is optionally substituted by OH, $CO_2$H, C(O)$NH_2$ or $NH_2$;
- $R^9$ is selected from the group consisting of —C(O)R, —C(O)NHR, —C(O)OR, —C(O)$CH_2$NRR', —C(O)$CH_2CH_2CO_2$R, —C(O)$CH_2SO_3$H, —C(O)—$(C_5H_4$N) and —$PO_3H_2$;
- each $R^{10}$ independently is selected from the group consisting of a bond and a linear or branched $(C_1$-$C_6)$alkyl; and
- each $R^{11}$ independently is selected from the group consisting of a hydrogen atom, a linear or branched $(C_1$-$C_6)$alkyl and an aryl, wherein the alkyl or aryl is optionally substituted by OH, $NH_2$, C(O)OH or C(O)NH;

or a pharmaceutically acceptable salt, stereoisomer or tautomer thereof.

17. The compound according to claim 16, wherein $L^2$ is linear or branched $(C_1$-$C_6)$alkylene.

18. The compound according to claim 16, selected from the group consisting of:
- 3-({4-hydroxy-1-[3-(2-methoxyphenyl)propanoyl]piperidin-4-yl}methyl)-3,4-dihydroquinazolin-4-one;
- 7-chloro-3-{[1-(2-ethylbutanoyl)-4-hydroxypiperidin-4-yl]methyl}-3,4-dihydroquinazolin-4-one;
- 3-({1-[2-(3-fluorophenoxy)acetyl]-4-hydroxypiperidin-4-yl}methyl)-3,4-dihydroquinazolin-4-one;
- 3-{[4-hydroxy-1-(2-methylpropanoyl)piperidin-4-yl]methyl}-6,7-dimethoxy-3,4-dihydroquinazolin-4-one;
- 3-{[4-hydroxy-1-(2-methylpropanoyl)piperidin-4-yl]methyl}-3,4-dihydroquinazolin-4-one;
- 4-hydroxy-1-([2-methyl-3-(thiophen-2-yl)propanoyl]piperidin-4-yl}methyl)-3,4-dihydroquinazolin-4-one;
- 7-chloro-3-{[1-(3-cyclopentylpropanoyl)-4-hydroxypiperidin-4-yl]methyl}-3,4-dihydroquinazolin-4-one;
- 3-{[1-(3-cyclopentylpropanoyl)-4-hydroxypiperidin-4-yl]methyl}-3,4-dihydroquinazolin-4-one;
- 7-chloro-3-{[4-hydroxy-1-(3-phenylpropanoyl)piperidin-4-yl]methyl}-3,4-dihydroquinazolin-4-one;
- 3-{[4-hydroxy-1-(3-phenylpropanoyl)piperidin-4-yl]methyl}-3,4-dihydroquinazolin-4-one;
- 7-chloro-3-({4-hydroxy-1-[2-methyl-3-(thiophen-2-yl)propanoyl]piperidin-4-yl}methyl)-3,4-dihydroquinazolin-4-one;
- 3-({4-hydroxy-1-[3-(thiophen-2-yl)propanoyl]piperidin-4-yl}methyl)-3,4-dihydroquinazolin-4-one;
- 3-{[1-(2-benzylpropanoyl)-4-hydroxypiperidin-4-yl]methyl}-3,4-dihydroquinazolin-4-one; and
- 3-{[1-(2-benzylpropanoyl)-4-hydroxypiperidin-4-yl]methyl}-7-chloro-3,4-dihydroquinazolin-4-one;

or a pharmaceutically acceptable salt, stereoisomer or tautomer thereof.

19. A combination comprising a compound according to claim 16 and one or more active agents selected from the group consisting of anti-cancer agents, neurological agents, thrombolytic agents, antioxidant agents, antidiabetes agents, antiinfective agents, antihypertensive agents, diuretic agents, immunosuppressive agents, cardiovascular agents, immunomodulatory agents, antiinflammatory agents, antiviral agents and antibacterial agents.

20. A method for inhibiting a deubiquitinating enzyme in a patient, comprising administering to a patient in need thereof a compound according to claim 16.

21. The method according to claim 20, wherein the deubiquitinating enzyme is ubiquitin specific protease 7 or herpes associated ubiquitin specific protease.

22. The method according to claim 20, wherein the patient suffers from a disease or disorder selected from the group consisting of cancer, metastasis, viral infectivity, viral latency, a viral infection and a viral disease.

23. The method according to claim 22, wherein the viral infection or viral disease is selected from the group consisting of Epstein-Barr virus, hepatitis A, hepatitis C, severe acute respiratory syndrome, poliomyelitis, herpes simplex type 1 viral infection, herpes simplex type 2 viral infection, coronavirus infection, rhinoviral infection, adenoviral infection, coronavirus disease, rhinoviral disease and adenoviral disease.

* * * * *

UNITED STATES PATENT AND TRADEMARK OFFICE
CERTIFICATE OF CORRECTION

PATENT NO. : 9,546,150 B2  
APPLICATION NO. : 14/241923  
DATED : January 17, 2017  
INVENTOR(S) : Colland et al.

Page 1 of 1

It is certified that error appears in the above-identified patent and that said Letters Patent is hereby corrected as shown below:

On the Title Page

Item [54], delete:
"SUBSTITUTED QUINAZOLIN-4-ONES FOR INHIBITING UBIQUITIN SPECIFIC PROTEASE 7"

Insert:
-- SUBSTITUTED QUINAZOLIN-4-ONES FOR INHIBITING UBIQUITIN SPECIFIC PROTEASE 7 AND THERAPEUTIC APPLICATIONS THEREOF --

Signed and Sealed this
Second Day of May, 2017

Michelle K. Lee
*Director of the United States Patent and Trademark Office*